(12) United States Patent
Liang

(10) Patent No.: US 7,271,276 B2
(45) Date of Patent: Sep. 18, 2007

(54) METAL COMPLEXES FOR CATALYTIC CARBON-CARBON BOND FORMATION

(75) Inventor: Lan-Chang Liang, Kaohsiung (TW)

(73) Assignee: National Sun Yat-Sen University (TW)

( * ) Notice: Subject to any disclaimer, the term of this patent is extended or adjusted under 35 U.S.C. 154(b) by 398 days.

(21) Appl. No.: 10/875,073

(22) Filed: Jun. 23, 2004

(65) Prior Publication Data

US 2005/0288505 A1 Dec. 29, 2005

(51) Int. Cl.
C07F 15/00 (2006.01)
C07F 9/02 (2006.01)
(52) U.S. Cl. .......................... 556/21; 556/174
(58) Field of Classification Search ............... 556/21, 556/174
See application file for complete search history.

(56) References Cited

U.S. PATENT DOCUMENTS 6,395,916 B1 5/2002 Buchwald et al.
6,562,989 B2 5/2003 Hartwig et al.
6,573,345 B1 6/2003 Bansleben et al.

OTHER PUBLICATIONS

Abstract, "Metal Complexes Containing Chelating Amidophosphine Ligands," 90NSYS5065036 www.datas.ncl.edu.tw Nov. 22, 2004.

Yin, Chi-Chun, *Metal Complexes Containing Chelating Amidophosine Ligands*, Sep. 11, 2002, pp. 2, 14 to 35, 37, 38, 42 and 43.
Wolfe, John P. et al. "Rational Development of Practical Catalysts for Aromatic Carbon-Nitrogen Bond Formation", *Acc. Chem. Res.* (1998), 31: 805-818.
Hartwig, John . "Carbon-Heteroatom Bond-Forming Reductive Eliminations of Amines, Ethers, and Sulfides", *Acc. Chem. Res.* (1998). 31: 852-860.
Sadighi, Joseph P. et al. "A Highly Active Palladium Catalyst System for the Arylation of Anilines", *Tetrahedron Letters* (1998), 39: 5327-5330.
Liang, Lan-Chang et al. "Amido Phosphine Complexes of Zinc", *Inorganic Chemistry* (2003), 42: 5471-5473.
Liang, Lan-Chang et al. "Nickel (II) Complexes of Bis(2-diphenylphosphinophenyl)amide", *Organometallics* (2003), 22(15): 3007-3009.
Liang, Lan-Chang et al. "Aluminum Complexes Incorporating Bidentate Amido Phosphine Ligands", *Inorganic Chemistry* (2004), 43: 2166-2174.
Huang, Mei-Hui and Lan-Chang Liang, "Amido Pincer Complexes of Palladium: Synthesis, Structure, and Catalytic Heck Reaction", *Organomettalics* (2004), 23: 2813-2816.
Liang, Lan-Chang et al. "Nickel(II) Complexes Containing Bidentate Diarylamido Phospine Ligands", *Organometallics*, (2004), sheets 1-10.

*Primary Examiner*—Porfirio Nazario-Gonzalez
(74) *Attorney, Agent, or Firm*—Ladas and Parry LLP

(57) ABSTRACT

The present invention relates to a complex comprising a novel and stable ligand and a metal center. The ligand contains a ring, particularly a phenyl group, or a hydrocarbon group which links an amino group and $PR^1R^2$, $NR^1R^2$, $OR^1$, $SR^1$, or $AsR^1R^2$ group such that the structure of the ligand can be stabilized.

38 Claims, 14 Drawing Sheets

METAL COMPLEXES FOR CATALYTIC CARBON-CARBON BOND FORMATION

BACKGROUND OF THE INVENTION

1. Field of the Invention

The present invention relates to metal complexes containing chelating ligands. The complex can be used for catalyzing carbon-carbon bond formation between saturated and saturated, saturated and unsaturated, and unsaturated and unsaturated bonds.

2. Description of the Related Art

Metal complexes are commonly used as catalysts for unusual chemical transformation in chemical industry, petrochemical industry, pharmaceutical industry, lubricant material and polymer material. One remarkable example in this aspect is the chelating amido phosphine derivatives that contain the —SiMe$_2$CH$_2$— ligand backbone as depicted in formula i.

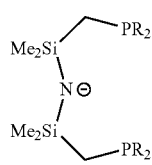

formula i

The tridentate ligands of this type have shown widespread reactivity with metals of the periodic table. These ligands, however, are prone to phosphine dissociation under certain circumstances due to the flexibility of the backbone. With the silyl linker, the ligands may become reactive, as cleavage of both N—Si and C—H bonds has been observed in the ligand depicted in formula i.

A ligand represented by the formula ii is disclosed in U.S. Pat. No. 6,395,916.

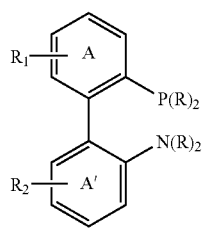

formula ii

The amino group and phosphine groups are located in different phenyl group for stabling the linkage of the ligand by the electrons in the phenyl group.

A ligand represented by the formula iii is disclosed in U.S. Pat. No. 6,562,989,

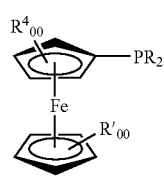

formula iii wherein the metal ion is linked to the two different rings for stabling the linkage of the ligand by the electrons in the rings.

Furthermore, a ligand represented by the formula iv is disclosed in U.S. Pat. No. 6,573,345,

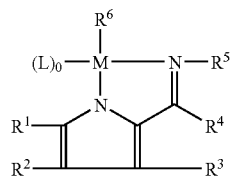

formula iv wherein the pyrrolyl group renders the linkage of the ligand stable. The ligand is mainly used for catalyzing olefin oligomerization and polymerization.

SUMMARY OF THE INVENTION

The present invention relates to a complex comprising a novel and stable ligand and a metal center. The ligand contains a ring, particularly a phenyl group, or a hydrocarbon group which links an amino group and PR$^1$R$^2$, NR$^1$R$^2$, OR$^1$, SR$^1$, or AsR$^1$R$^2$ group such that the structure of the ligand can be stabilized.

The metal complex comprises a ligand L and a metal center M$^1$,
wherein
M$^1$ is selected from the group consisting of transition metal, Li, Na, K, Mg, Ca, Al, and Ga; and
the ligand L is represented by the following general formula I

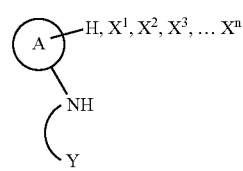

formula I wherein:

A represents a ring or heterocyclic ring, and said ring or heterocyclic ring is unsubstituted or substituted with X$^1$ to X$^n$;

X$^1$ to X$^n$, for each occurrence independently represent one or more groups selected from the group consisting of hydrocarbons, PR$^1$R$^2$, NR$^1$R$^2$, OR$^1$, SR$^1$, and AsR$^1$R$^2$;

Y represents a group selected from the group consisting of PR$^1$R$^2$, NR$^1$R$^2$, OR$^1$, SR$^1$, and AsR$^1$R$^2$;

n represents an integer larger than or equal to 1;

R$^1$ and R$^2$ for each occurrence independently represent saturated or unsaturated hydrocarbon or aromatic groups with or without heteroatoms of O, S, N, P or As; and the linkage between N—Y is a saturated or unsaturated hydrocarbon or aromatic group with or without substituents.

The present invention also provides a method for synthesizing the complex comprising reacting M$^1$E and the ligand L to form the complex:

scheme VII

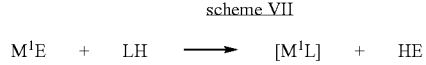

wherein:

E represents alkyl, aryl, amide, or alkoxide group.

DETAILED DESCRIPTION OF THE INVENTION

The ligand L according to the invention is represented by the following general formula I.

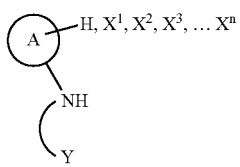

formula I

A represents a ring or heterocyclic ring, and said ring or heterocyclic ring is unsubstituted or substituted with $X^1$ to $X^n$. If A is an unsubstituted ring, A is only linked to hydrogen atom. In one preferred embodiment, A is an unsubstituted or substituted heterocyclic ring comprising N, O, S, or P atom. In another preferred embodiment, A is an unsubstituted or substituted aromatic ring. In another aspect, A is preferably a five or six membered ring or a five or six membered heterocyclic ring. In still another aspect, A is a bicyclic or polycyclic ring. In still another preferred embodiment, A is an unsubstituted ring. In one more preferred embodiment, A is an unsubstituted or substituted phenyl group.

According to the invention, when A is a substituted ring, the substituents are $X^1$ to $X^n$. $X^1$ to $X^n$, for each occurrence independently represent one or more groups selected from the group consisting of hydrocarbons, $PR^1R^2$, $NR^1R^2$, $OR^1$, $SR^1$, and $AsR^1R^2$; and preferably, $X^1$ to $X^n$ are $PR^1R^2$.

In formula I, Y represents a group selected from the group consisting of $PR^1R^2$, $NR^1R^2$, $OR^1$, $SR^1$, and $AsR^1R^2$; and preferably, Y is $PR^1R^2$.

In one embodiment of the invention, $X^1$ to $X^n$ and Y are all $PR^1R^2$.

In formula I, n represents an integer larger than or equal to 1. If A has the substituents $X^1$ to $X^n$, n represents the number of the substituents. Preferably, n is equal to 1.

In the substituents, $R^1$ and $R^2$ for each occurrence independently represent saturated or unsaturated hydrocarbon or aromatic groups with or without heteroatoms of O, S, N, P or As. In one preferred embodiment of the invention, $R^1$ and $R^2$ for each occurrence independently represent phenyl group with or without substituents.

In formula I, the linkage between N—Y is a saturated or unsaturated hydrocarbon or aromatic group with or without substituents; and preferably, the linkage between N—Y is an alkyl with or without substituents; and more preferably, when the linkage between N—Y is saturated, it is ethyl or propyl group with or without substituent; and when the linkage between N—Y is unsaturated, it is phenyl group with or without substituents.

The ligand according to the invention is a monoanion when H atom is absent from NH.

Figure 3:
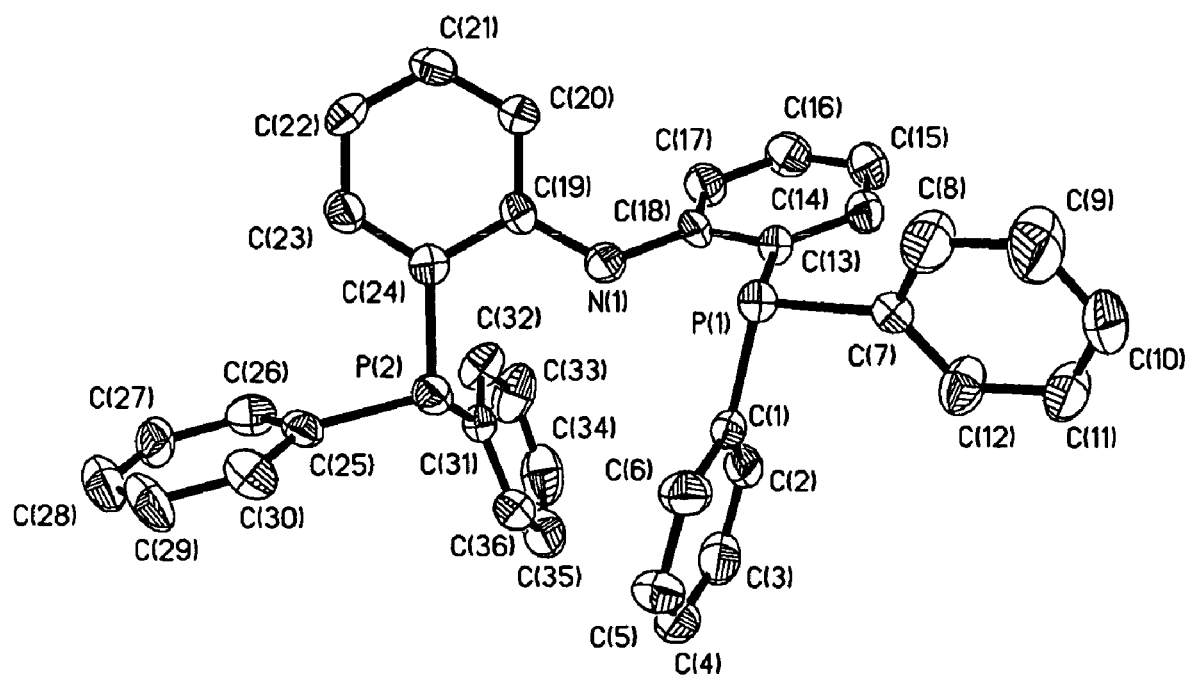
FIG. 3 illustrates the molecular structure of bis(2-diphenylphosphinophenyl)amine (H[PNP]) represented by formula Ia.

In one preferred embodiment of the invention, the ligand is bis(2-diphenylphosphinophenyl)amine (H[PNP]) represented by the following formula Ia:

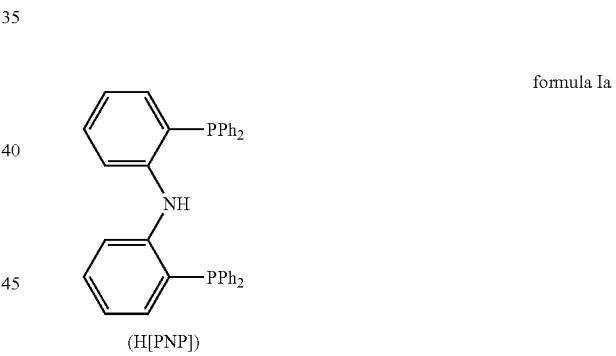

formula Ia (H[PNP])

wherein Ph represents phenyl group. The molecular structure of H[PNP] is shown in FIG. 3.

In another preferred embodiment of the invention, the ligand is N-(2-diphenylphosphinophenyl)-2,6-diisopropylaniline (H[NP], H[$^i$Pr-NP]) or N-(2-diphenylphosphinophenyl)-2,6-dimethylaniline (H[Me-NP]) represented by the following formula Ib:

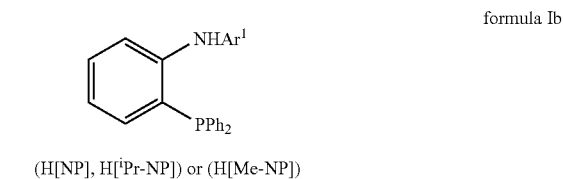

formula Ib (H[NP], H[$^i$Pr-NP]) or (H[Me-NP])

wherein:

Ar$^1$ represents 2,6-C$_6$H$_3^i$Pr$_2$ or 2,6-C$_6$H$_3$Me$_2$;

Ph represents phenyl group; and $^i$Pr represents isopropyl group.

Figure 1:
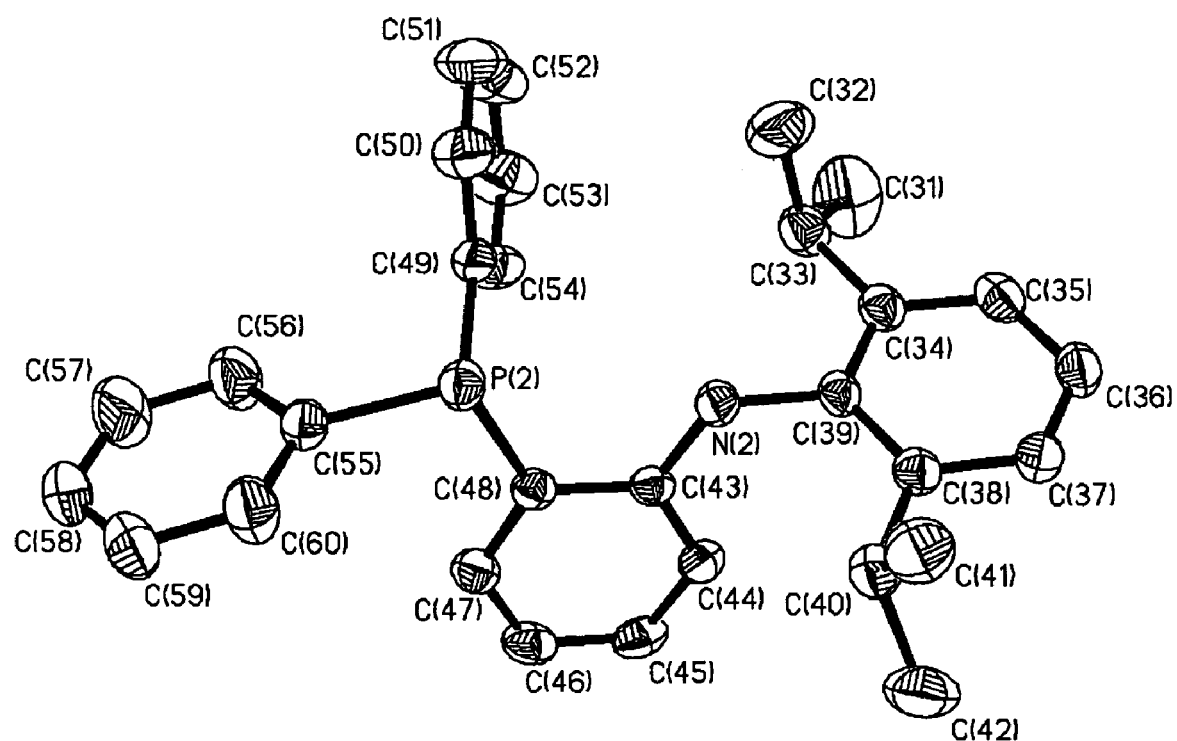
FIG. 1 illustrates the molecular structure of N-(2-diphenylphosphinophenyl)-2,6-diisopropylaniline (H[NP], H[$^i$Pr-NP]) represented by formula Ib.
Figure 4:
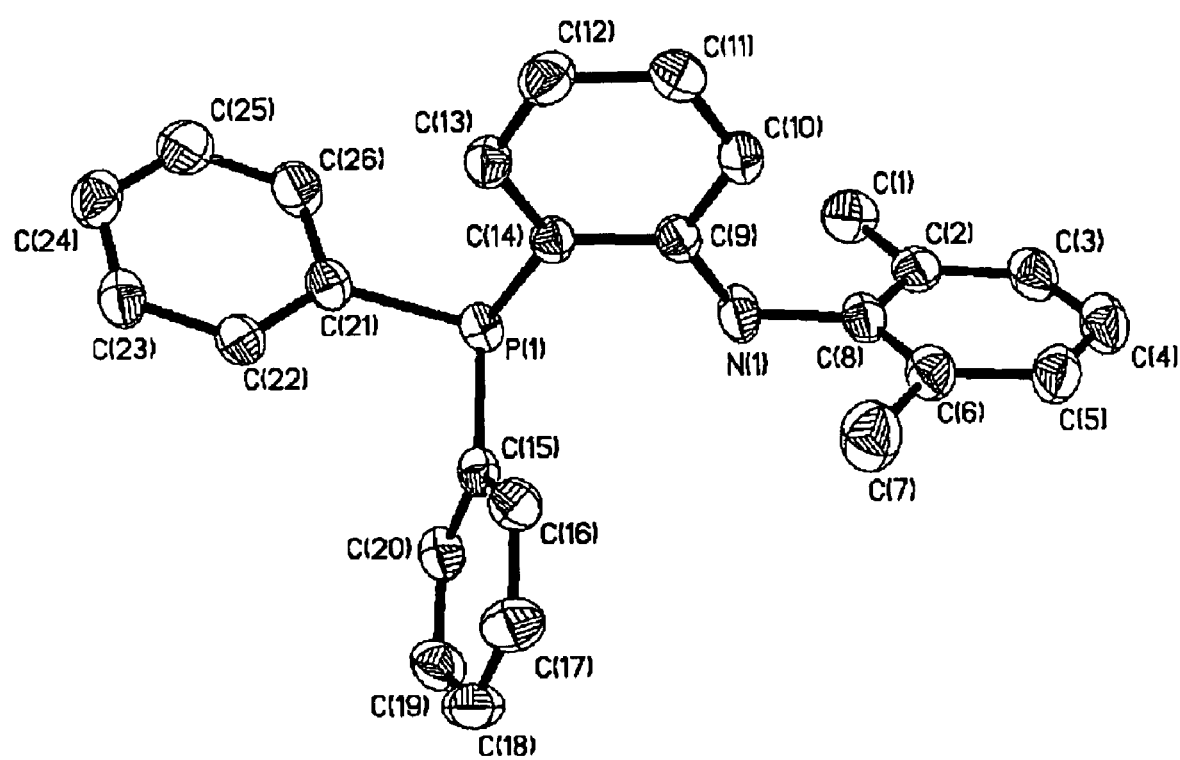
FIG. 4 illustrates the molecular structure of N-(2-diphenylphosphinophenyl)-2,6-dimethylaniline (H[Me-NP]) represented by formula Ib.

The molecular structure of H[NP] or H[$^i$Pr-NP] is shown in FIG. 1 and the molecular structure of H[Me-NP] is shown in FIG. 4.

The invention also provide a method for synthesizing the ligand L comprising the steps of:

(a) conducting a cross-coupling reaction of a bromine or iodine substituted fluoride represented by the following formula II and a fluorine substituted amine represented by the following formula III to form an amine with multiple fluorine substituents represented by the following general formula IV; and Scheme I

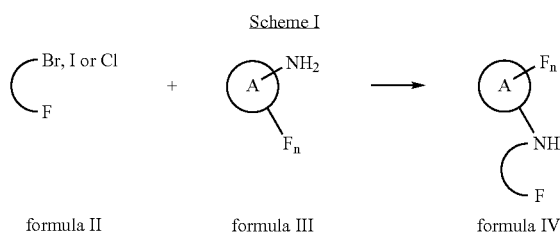

formula II      formula III      formula IV (b) conducting a nucleophilic reaction of the amine with multiple fluorine substituents represented by the general formula IV, M$^2$X$^1$ to M$^2$X$^n$ and M$^2$y to form the ligand represented by the formula I;

wherein:

the linkage between fluorine and bromine or iodine of the fluoride represented by formula II is a saturated or unsaturated hydrocarbon or aromatic group with or without substituents;

M$^2$ is a metal selected from the group consisting of Li, Na and K; and wherein preferably is K; and A, n, X$^1$ to X$^n$ and Y are as defined in ligand L.

One embodiment of the method is depicted below:

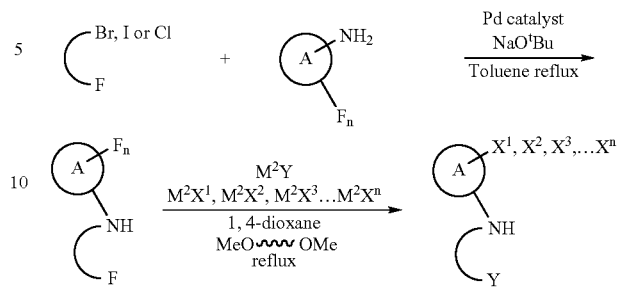

The ligand synthesis includes two straightforward steps from relatively inexpensive, commercially available starting materials.

According to the invention, step (a) is a palladium-catalyzed cross-coupling reaction in the presence of sodium tert-butoxide in refluxing toluene to produce the intermediate represented by formula IV. The number and position of the substituent F of A in the starting material depends on that of the X$^n$ substituent in the desired final product. Palladium catalyst is a common catalyst for use in synthesis (Wolfe, J. P.; Wagaw, S.; Marcoux, J. F.; Buchwald, S. L. *Acc. Chem. Res.* 1998, 31, 805☐ Hartwig, J. F. Acc. Chem. Res. 1998, 31, 852☐Sadighi, J. P.; Harris, M. C.; Buchwald, S. L. *Tetrahedron Lett.* 1998, 39, 5327.). In one embodiment of the invention, palladium catalyst comprises Pd(OAc)$_2$ and [2-(diphenylphosphino)phenyl]ether (DPEphosbis).

Step (b) of the method comprises reacting the intermediate represented by formula IV, M$^2$X$^1$ to M$^2$X$^n$ and M$^2$Y in 1,4-dioxane or MeO—CH$_2$CH$_2$-MeO refluxing to obtain the final product represented by formula I.

In one embodiment of the invention, the method comprises the steps of:

(a) conducting a cross-coupling reaction of 2-fluoroaniline and 1-bromo-2-fluorobenzene to form di(2-fluorophenyl)amine in the presence of Pd catalyst and sodium tert-butoxide; and (b) reacting di(2-fluorophenyl)amine and KPPh$_2$ to form the ligand bis(2-diphenylphosphinophenyl) amine (H[PNP]) in the presence of 1,4-dioxane.

The method for the synthesis of H[PNP] is depicted below, wherein Ph represents phenyl group.

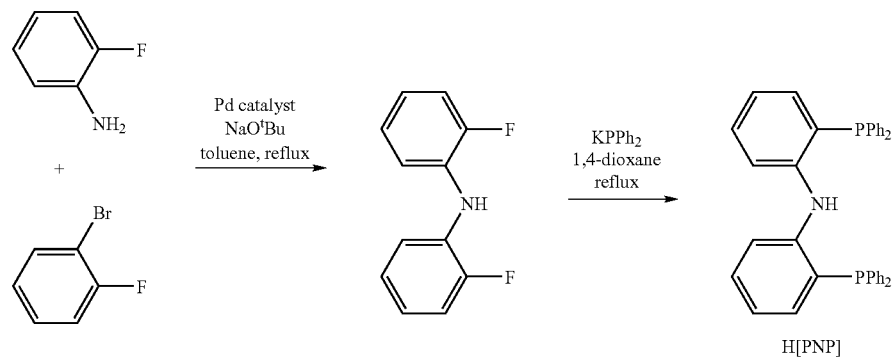

H[PNP]

The present invention provides a second method for synthesizing the ligand L comprising the steps of:
(a) conducting a cross-coupling reaction of a bromine, iodine or chloride substituted fluoride represented by the following formula IX and a substituted amine represented by the following formula X to form a compound represented by the following formula XI according to scheme IV; and

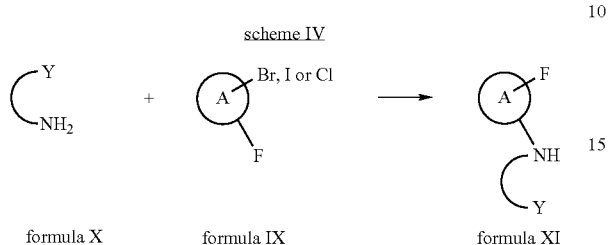

formula X    formula IX    formula XI (b) conducting a nucleophilic reaction of the compound represented by the general formula $X^1$, $M^2X^1$ to $M^2X^1$ and $M^2Y$ to form the ligand represented by the formula I;
wherein:
the linkage between Y and $NH_2$ of the amine represented by formula X is a saturated or unsaturated hydrocarbon or aromatic group with or without substituents; and
A, n, $X^1$ to $X^n$ and Y are as defined in ligand L.

In one embodiment of the invention, the second method comprises the steps of:
(a) conducting a cross-coupling reaction of 1-bromo-2-fluorobenzene and $Ar^3NH_2$ to form N-(2-fluorophenyl)$NHAr^3$ in the presence of Pd catalyst and sodium tert-butoxide; and
(b) reacting N-(2-fluorophenyl)$NHAr^3$ and $KPPh_2$ to form the ligand N-(2-diphenylphosphinophenyl)$NHAr^3$ in the presence of 1,4-dioxane or DME;
wherein
$Ar^3$ represents 2,6-diisopropyllaniline or 2,6-dimethyla-niline; and
Ph represents phenyl group.

The method for the synthesis of H[NP] is depicted below, wherein Ph represents phenyl group:

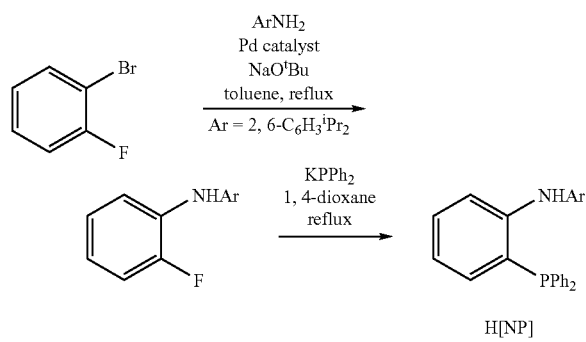

A third method for synthesizing the ligand L according to the present invention comprises the steps of:
(a) conducting a cross-coupling reaction of a compound represented by the following formula XII and a compound represented by the following formula XIII to form a compound represented by the following formula XIV according to scheme V; and

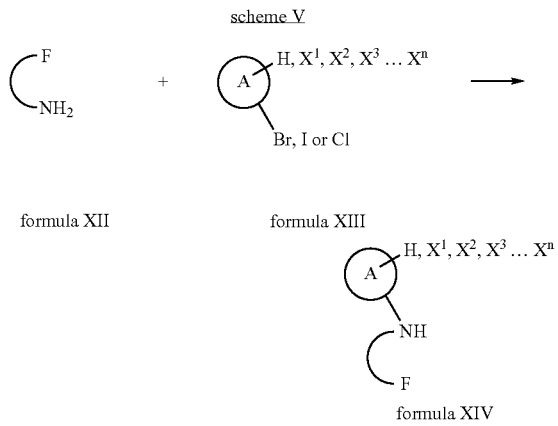

formula XII    formula XIII formula XIV (b) conducting a nucleophilic reaction of the compound represented by the general formula XIV and $M^2Y$ to form the ligand represented by the formula I;
wherein:
the linkage between F and $NH_2$ of the compound represented by formula XII is a saturated or unsaturated hydrocarbon or aromatic group with or without substituents; and
A, n, $X^1$ to $X^n$ and Y are as defined in ligand L.

The present invention also provide a fourth method for synthesizing the ligand L comprising the steps of:
(a) conducting a cross-coupling reaction of a substituted amine represented by the following formula X and a compound represented by the following formula XV to form a compound represented by the following formula XVI according to scheme VI; and

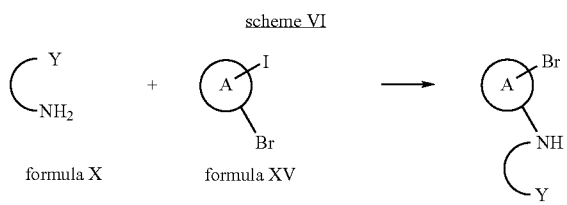

formula X    formula XV (b) reacting the compound represented by the general formula XVI with a base and then with $Hal^5X^1$ to $Hal^5X^n$ to form the ligand represented by the formula I;
wherein:
the linkage between Y and $NH_2$ of the amine represented by formula X is a saturated or unsaturated hydrocarbon or aromatic group with or without substituents;
$Hal^5$ represents halogen; and
A, n, $X^1$ to $X^n$ and Y are as defined in ligand L.

According to the fourth method of the invention, the base is preferably BuLi, $^iPrMgCl$ or Mg, wherein $^iPr$ represents isopropyl group.

The ligand L can complex with a metal center $M^1$ to form a chelated complex. $M^1$ is selected from the group consisting of transition metal, Li, Na, K, Mg, Ca, Al, and Ga; and preferably, $M^1$ is selected from the group consisting of Zn, Pd, Al, and Ni.

In one embodiment of the invention, the ligand is coordinated to the metal center through two coordinate bonds. One of the coordinate bond is between $M^1$ and N and the other is between M¹ and Y. The complex is represented by the following general formula V:

L_bM¹Z¹                formula V wherein:
the number of ligand L is b;
the number of Z¹ is c;
the number of the coordination number of M¹ is a; and
Z¹ is coordinated to metal M¹ through d coordinate bonds;
Z¹ represents a group; and wherein preferably, Z¹ is selected from the group consisting of an unsubstituted or substituted hydrocarbon group, unsubstituted or substituted aromatic group, halogen group and ligand L; and more preferably, Z¹ represents ligand L;
2b+cd≦a; and
the linkage between L and M¹ is represented by the following general formula Va:

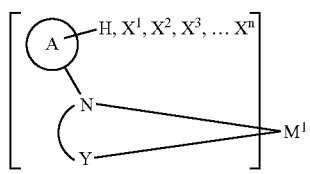
formula Va

In one embodiment of the invention, the complex is represented by the following formula Vb;

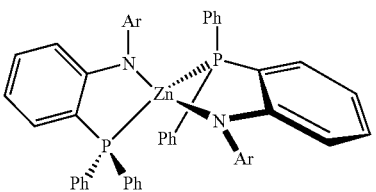

wherein:
Ar² represents 2,6-C₆H₃^iPr₂;
Ph represents phenyl group; and
^iPr represents isopropyl group.

In one embodiment of the invention, the complex is represented by the following formula Vc:

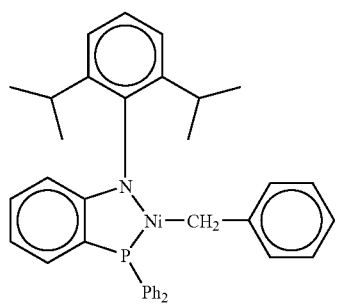
Formula Vc wherein Ph represents phenyl group.

In another embodiment of the invention, the complex is represented by the following formula Vd:

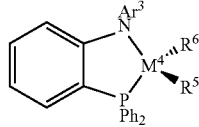
formula Vd wherein
Ar³ represents 2,6-C₆H₃^iPr₂ or 2,6-C₆H₃Me₂;
^iPr represents isopropyl group;
R⁵ and R⁶ independently represent methyl group, ethyl group, CH₂SiMe₃, phenyl group, PMe₃, or halogen; and R⁵ and R⁶ taken together optionally represent the group represented by the following formula VII; and

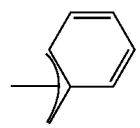
formula VII

Figure 5:
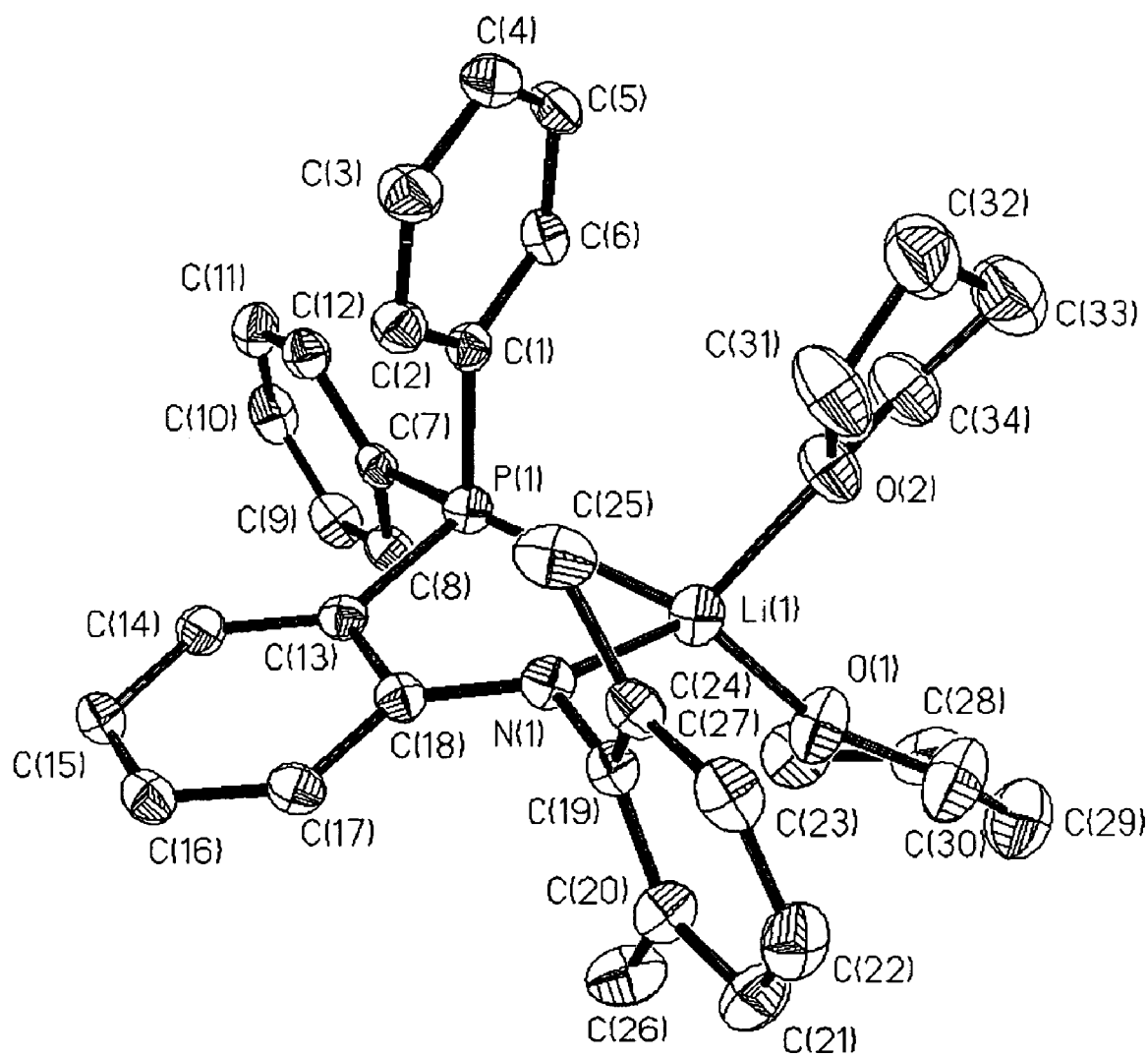
FIG. 5 illustrates the molecular structure of [Me-NP]Li $(THF)_2$.
Figure 6:
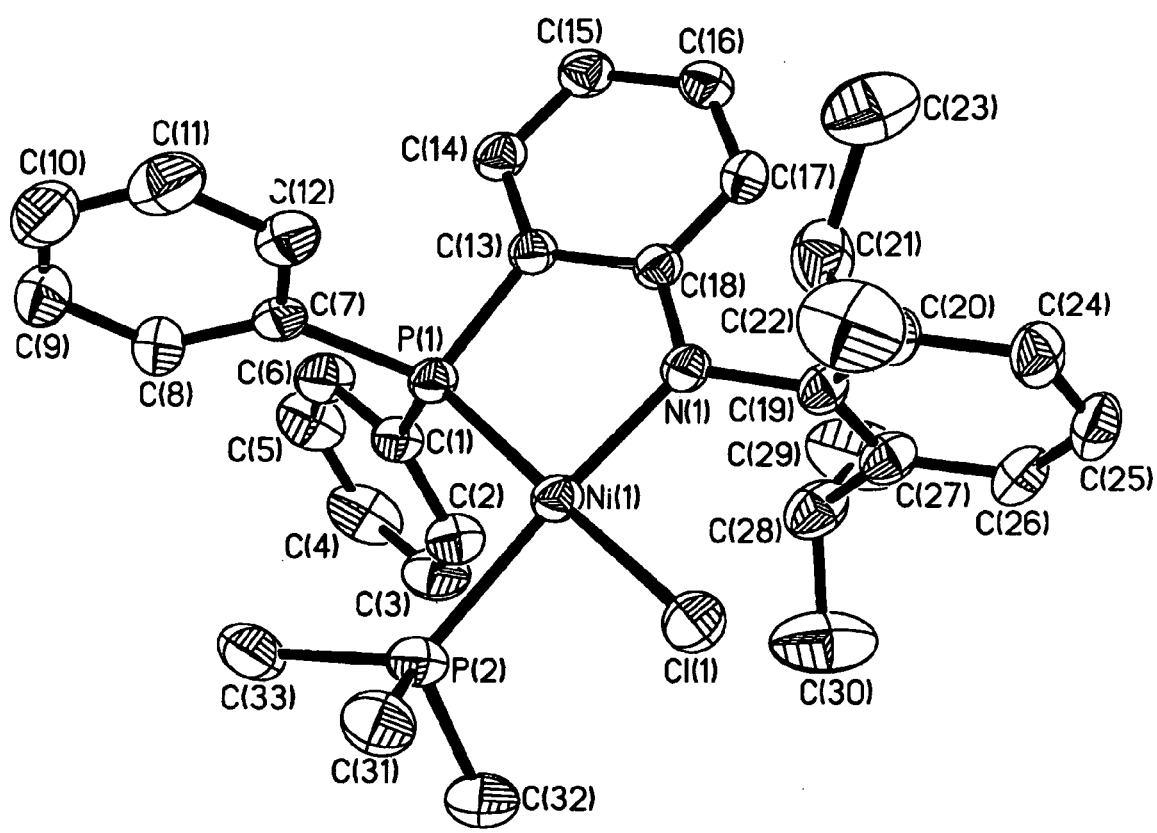
FIG. 6 illustrates the molecular structure of [$^i$Pr-NP]NiCl $(PMe_3)$.
Figure 7:
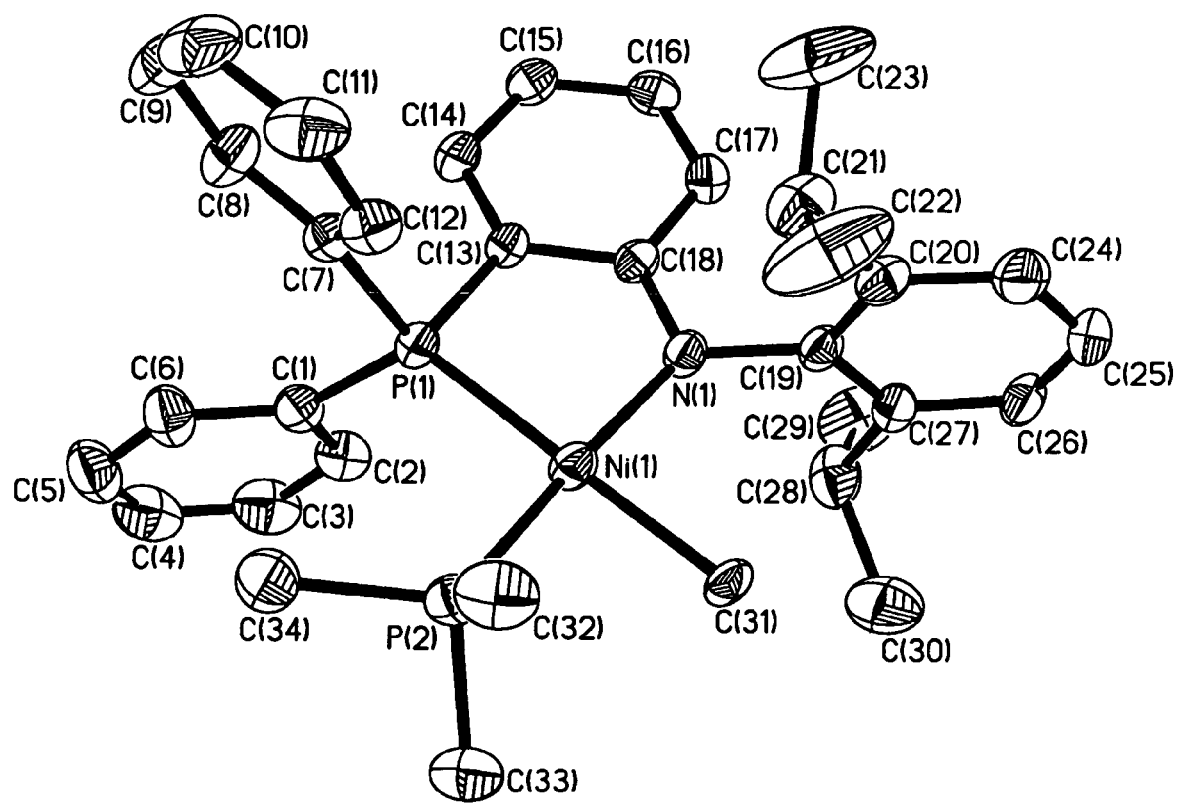
FIG. 7 illustrates the molecular structure of [$^i$Pr-NP]NiMe $(PMe_3)$.
Figure 8A:
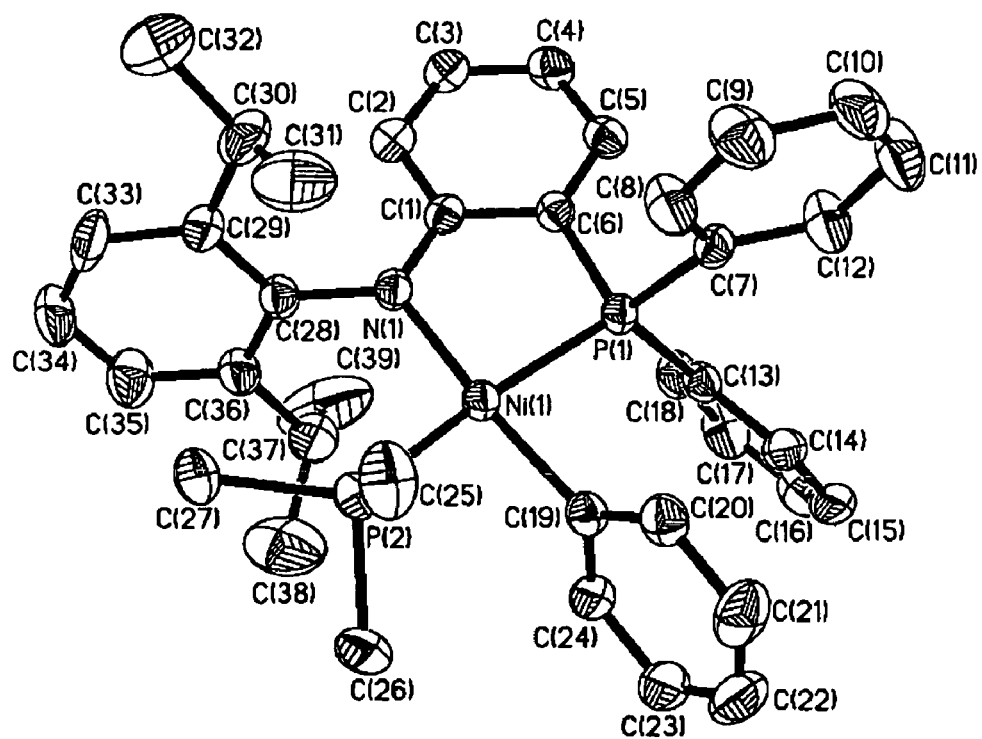
FIG. 8 illustrates two views of the molecular structure of [$^i$Pr-NP]NiPh$(PMe_3)$.
Figure 8B:
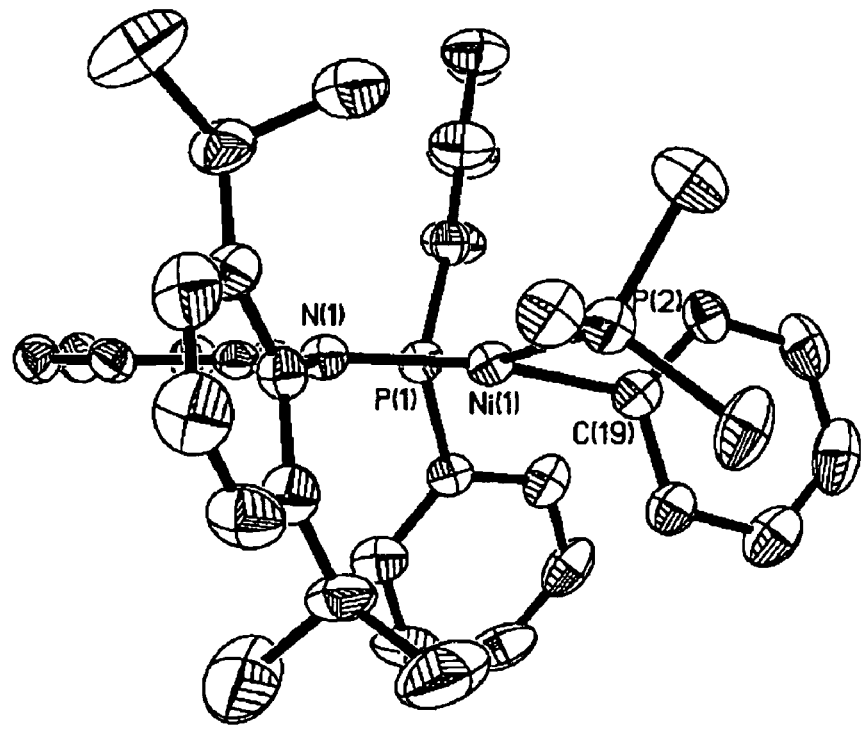
Figure 9:
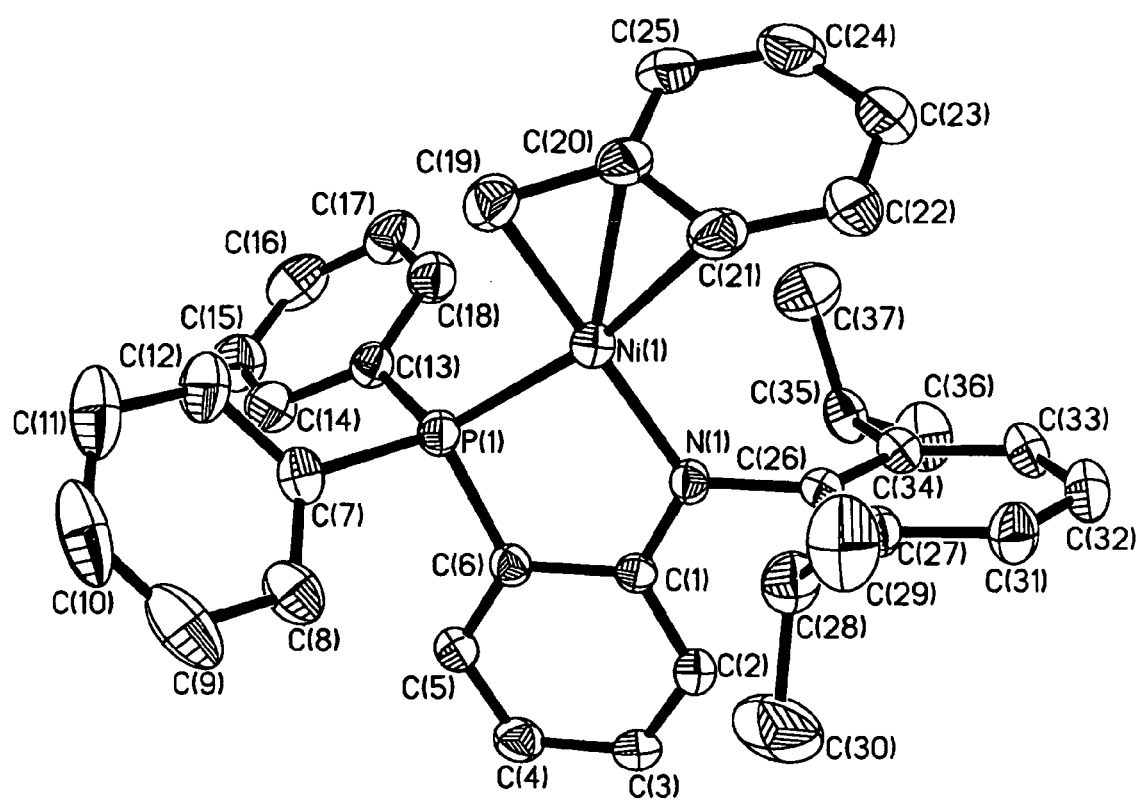
FIG. 9 illustrates the molecular structure of [$^i$Pr-NP]Ni $(\eta^3\text{-}CH_2\beta h)$.
Figure 10:
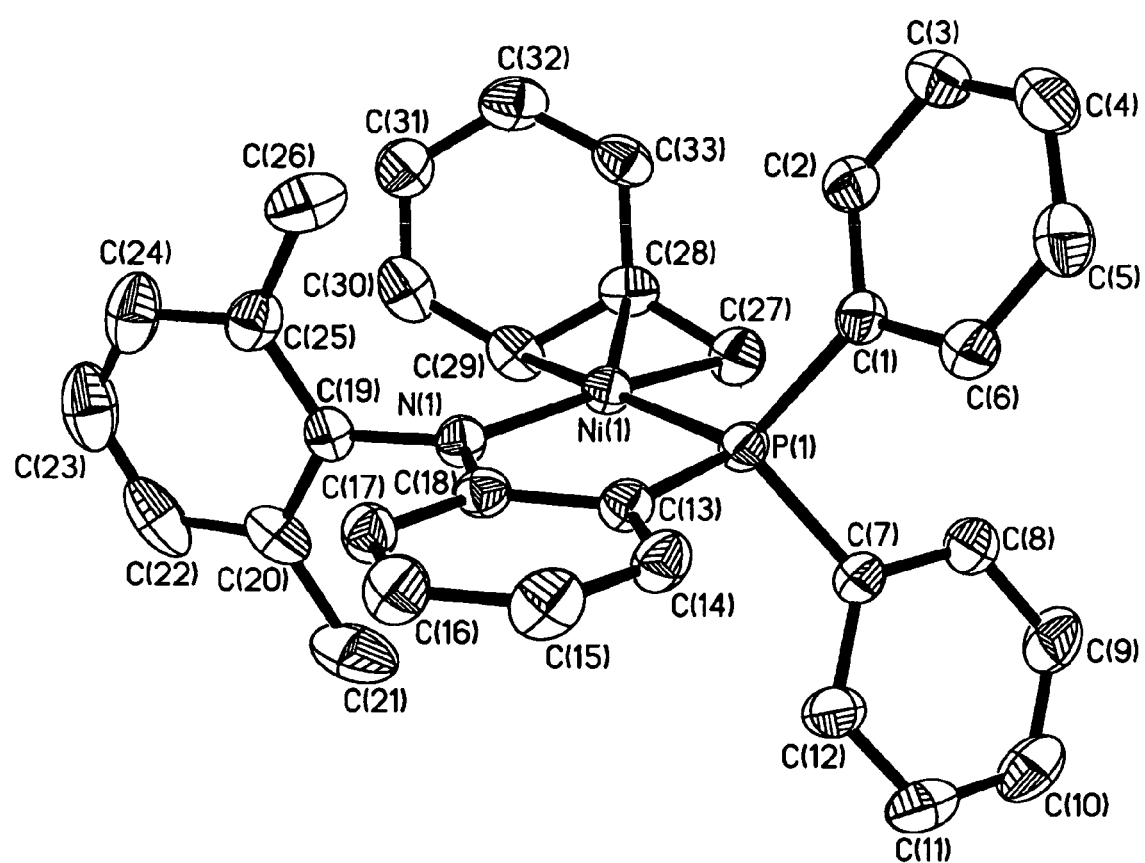
FIG. 10 illustrates the molecular structure of [Me-NP]Ni $(\eta^3\text{-}CH_3\text{-}Ph)$.
Figure 11:
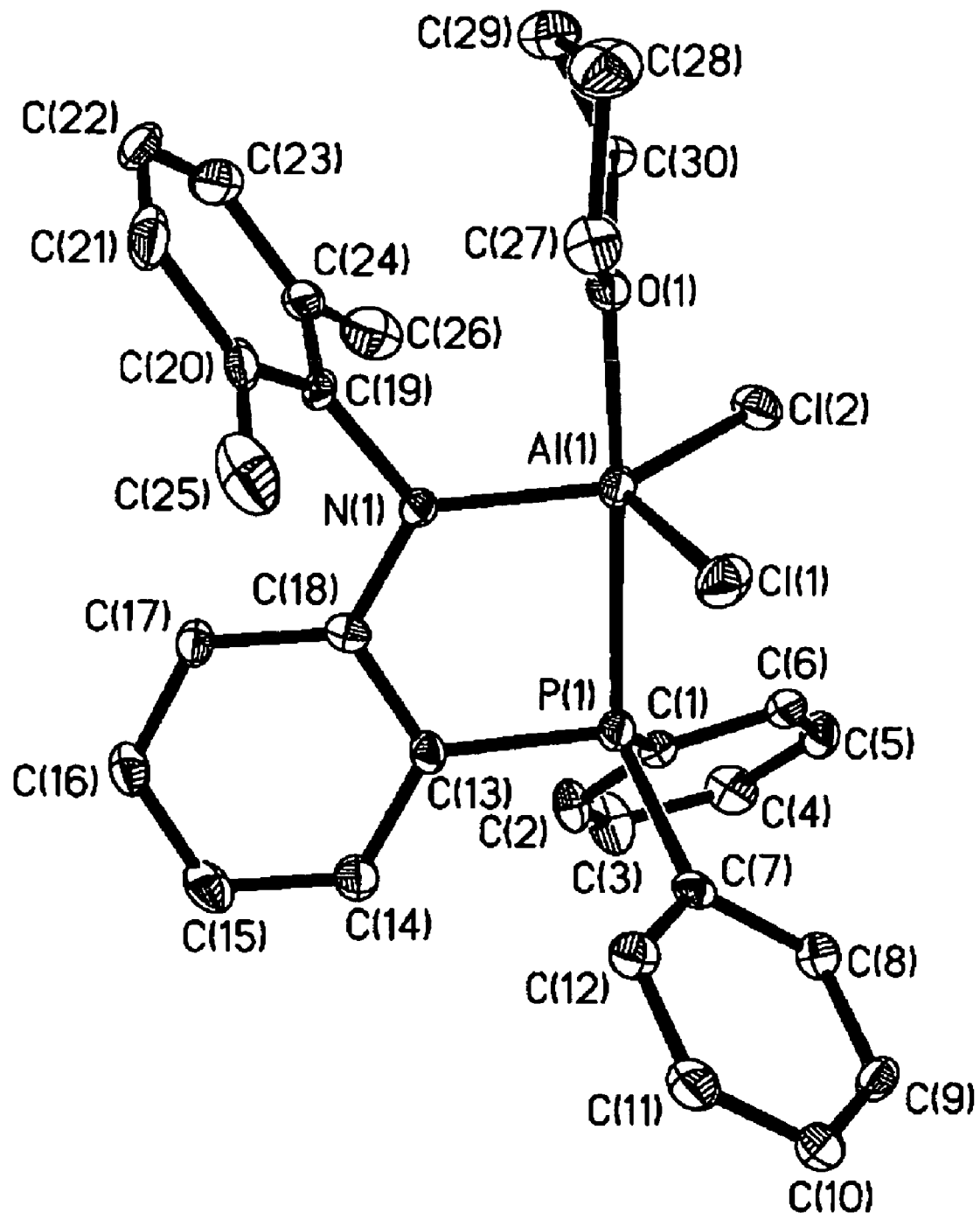
FIG. 11 illustrates the molecular structure of [Me-NP] $AlCl_2$ (THF).
Figure 12:
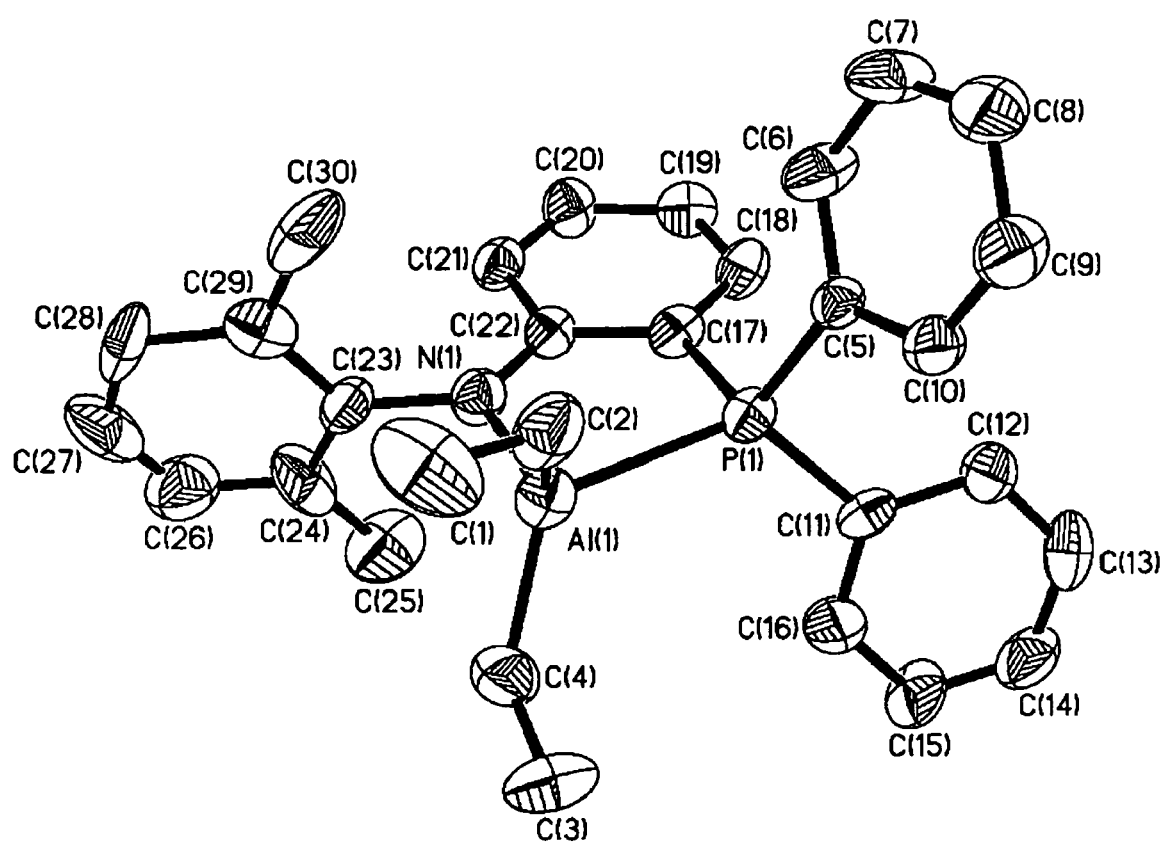
FIG. 12 illustrates the molecular structure of [Me-NP] $AlEt_2$.
Figure 13:
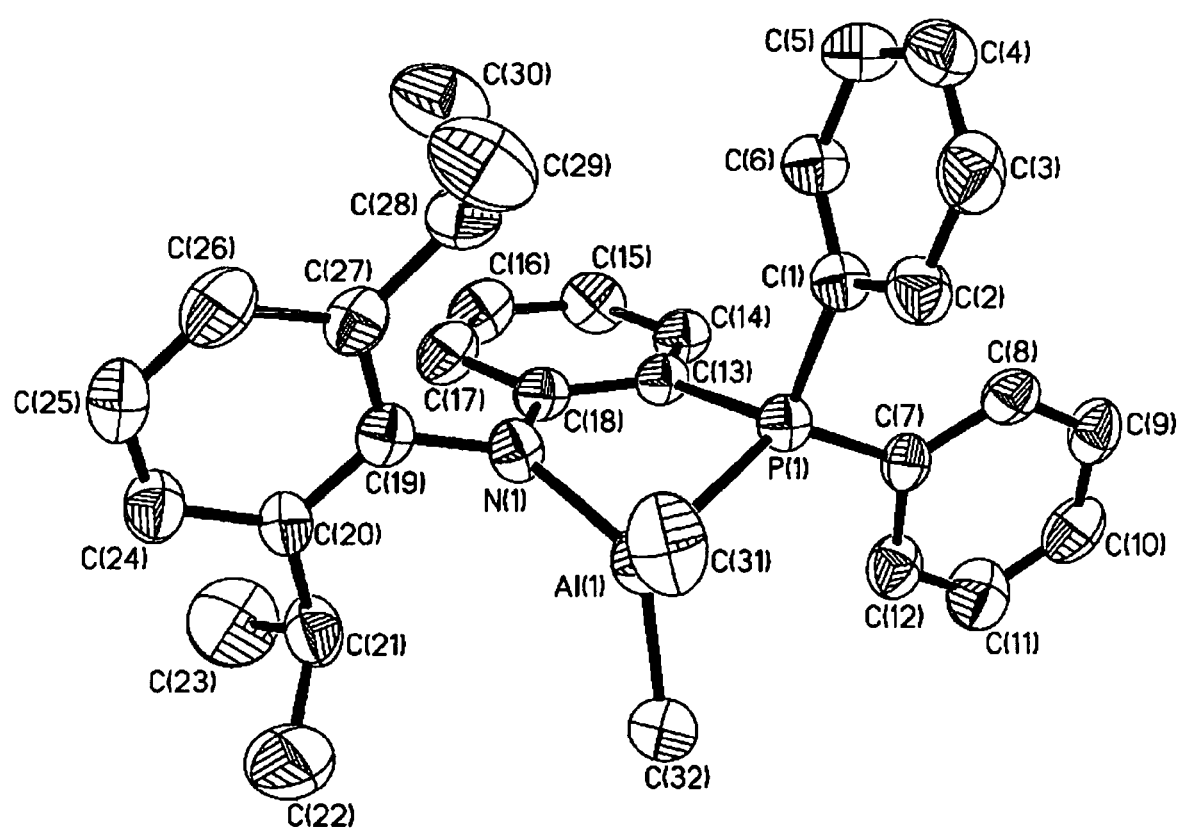
FIG. 13 illustrates the molecular structure of [$^i$Pr-NP] $AlMe_2$.

M⁴ represents the metal center of Ni or Al.
The molecular structure of [Me-NP]Li(THF)₂ is shown in FIG. 5.
The molecular structure of [^iPr-NP]NiCl(PMe₃) is shown in FIG. 6.
The molecular structure of [^iPr-NP]NiMe(PMe₃) is shown in FIG. 7.
The molecular structure of [^iPr-NP]NiPh(PMe₃) is shown in FIG. 8.
The molecular structure of [^iPr-NP]Ni(η³-CH₂Ph) is shown in FIG. 9.
The molecular structure of [Me-NP]Ni(η³-CH₃-Ph) is shown in FIG. 10.
The molecular structure of [Me-NP]AlCl₂ (THF) is shown in FIG. 11.
The molecular structure of [Me-NP]AlEt₂ is shown in FIG. 12.
The molecular structure of [^iPr-NP] AlMe₂ is shown in FIG. 13.

In another embodiment of the invention, the ligand is coordinated to the metal center through three coordinate bonds. One of the coordinate bond is between M¹ and N, the other is between M¹ and Y; another is between M¹ and the substituent X. The complex is represented by the following general formula VI:

L_eM¹Z²_f                formula VI wherein:
the number of ligand L is e;
the number of Z² is f
the number of the coordination number of M¹ is a; and
Z² is coordinated to metal M¹ through g coordinate bonds;
Z² represents a group; and wherein preferably, Z² is selected from the group consisting of an unsubstituted or substituted hydrocarbon group, unsubstituted or substituted aromatic group, halogen group and ligand L; more preferably, Z² represents ligand L;
3e+fg≦a; and the linkage between L and M¹ is represented by the following general formula VIa:

formula Va

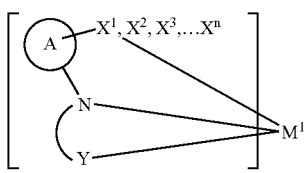

In one embodiment of the invention, the complex is represented by the following general formula VIb;

formula VIb

Figure 14:
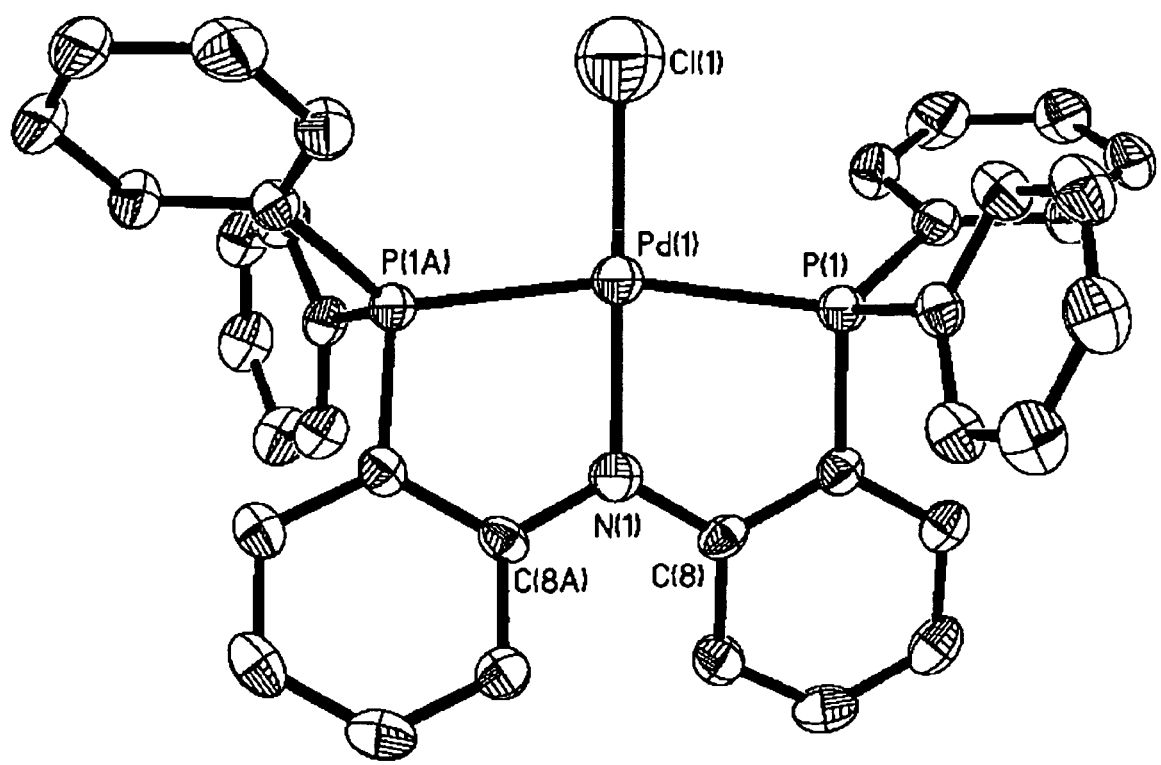
FIG. 14 illustrates the molecular structure of [PNP]PdCl.

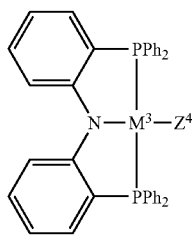

wherein
M³ represents Ni or Pd;
Z⁴ represents a group; and preferably, Z⁴ is selected from the group consisting of an unsubstituted or substituted hydrocarbon group, unsubstituted or substituted aromatic group, and halogen group; and more preferably, Z⁴ is selected from methyl, ethyl, n-butyl, i-butyl, $CH_2SiMe_3$, Cl, OAc and phenyl group; and
Ph represents phenyl group.
The molecular structure of [PNP]PdCl is shown in FIG. 14.

The synthesis of the complex comprising the ligand of the invention is well known to the artisans skilled in this field.

For example, a method for synthesizing the complex according to the invention comprises reacting M¹E and the ligand L to form the complex as depicted below:

scheme VII

M¹E + LH ⟶ [M¹L] + HE wherein:
E represents alkyl, aryl, amide, or alkoxide group.
In one embodiment, the method comprises the steps of:
(a) reacting M⁵E and the ligand to eliminate HE and form the complex [M⁵L]; and scheme VIII

M⁵E + LH ⟶ [M⁵L] + HE (b) reacting [M⁵L] and M¹Hal⁶ to form [M¹L];
wherein:
M⁵ is selected from the group consisting of transition metal, Li, Na, K, Mg, Ca, Al, and Ga Li, Na, K, Zn, Fe, Co, Ni, Al, Ru, Rh, Pd, Os, Ir, and Pt;
E represents alkyl, aryl, amide, or alkoxide group; and
Hal⁶ represents halogen.
In another embodiment, the method comprises the steps of:
(a) reacting the ligand L and M¹Z³ to form LM¹Z³ in the presence of diethyl ether or THF; and
(b) reacting the ligand L and LM¹Z³ by heating to form $L_2M^1$,
wherein Z³ represents a group; preferably, Z³ is selected from the group consisting of an unsubstituted or substituted hydrocarbon group, or unsubstituted or substituted aromatic group, and halogen group; and more preferably, Z³ is methyl group or ethyl group.
A method for use in synthesizing the complex represented by formula Vb is shown in the following scheme. The method comprises the steps of:
(a) reacting N-(2-diphenylphosphinophenyl)-2,6-diisopropylaniline H[NP] and ZnZ³ to form [NP]ZnZ³ in the presence of diethyl ether or THF; and
(b) reacting N-(2-diphenylphosphinophenyl)-2,6-diisopropylaniline (H[NP]) and [NP]ZnZ³ by heat to form [NP]₂Zn,
wherein Z³ represents a group; preferably, Z³ is selected from the group consisting of an unsubstituted or substituted hydrocarbon group, or unsubstituted or substituted aromatic group, and halogen group; and more preferably, Z³ is methyl group or ethyl group.

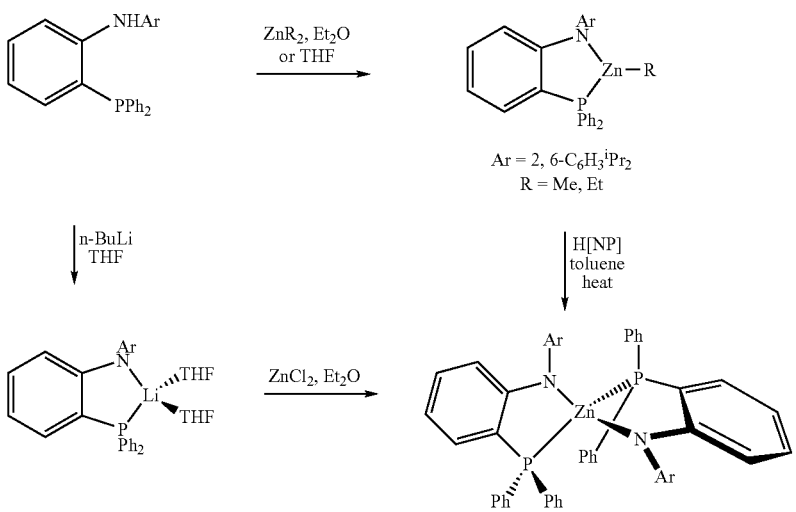

Preferably, step (b) is conducted in toluene refluxing.

Figure 2:
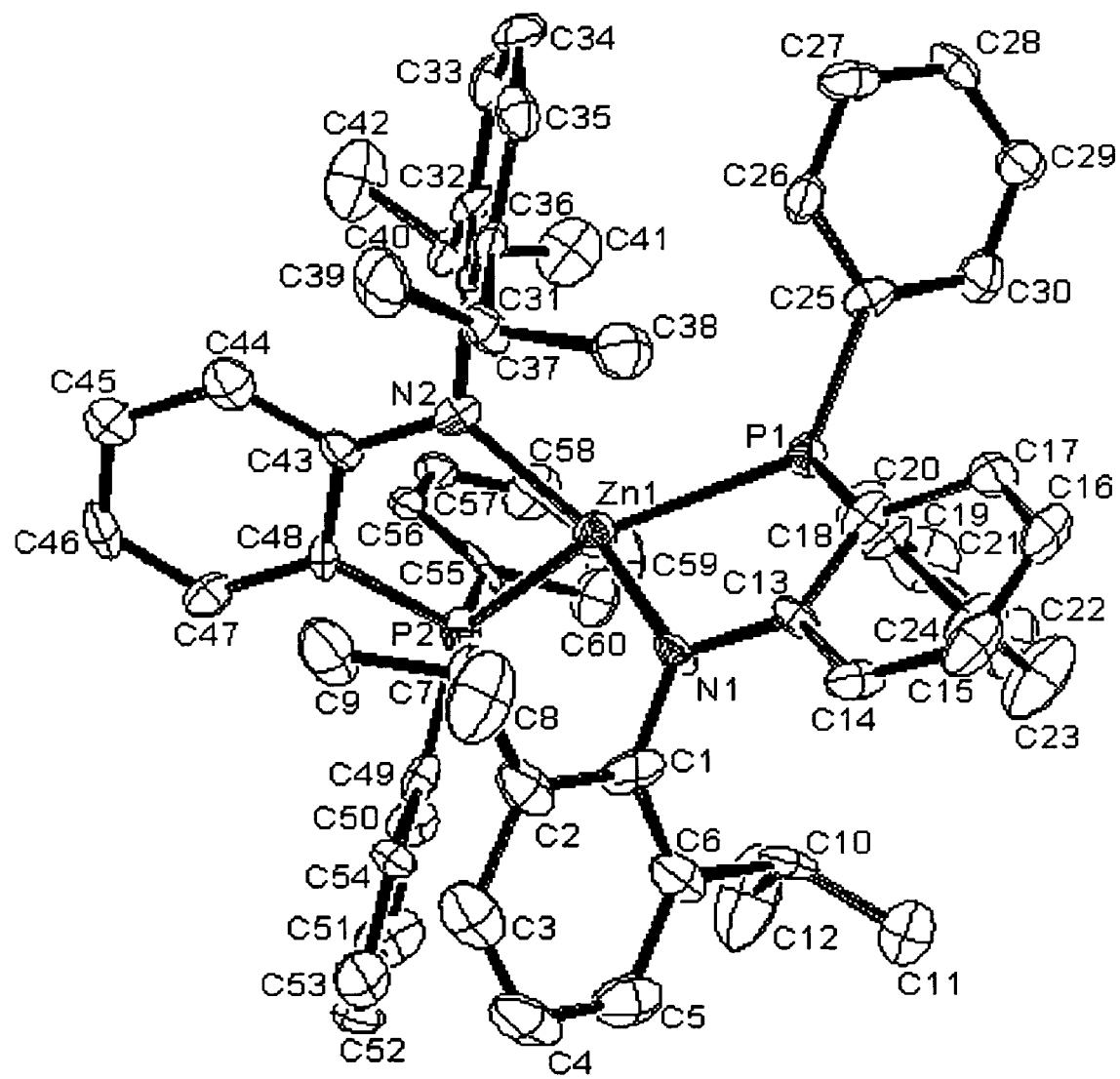
FIG. 2 illustrates the molecular structure of $[NP]_2Zn$ represented by formula Ia.

The molecular structure of [NP]$_2$Zn is shown in FIG. 2.

A second method for synthesizing the complex according to the invention comprises the steps of:
(a) reacting the ligand L and n-butyllithium to form LLi(THF)$_2$ in the presence of THF; and
(b) reacting LLi(THF)$_2$ and M$^1$Cl$_2$ to form LM$^1$.

A third method for synthesizing the complex according to the invention comprises the steps of:
(a) reacting the ligand L and n-butyllithium to form LLi(THF)$_2$ in the presence of THF;
(b) reacting LLi(THF)$_2$ and M$^1$Cl$_2$(DME) to form LM$^1$Cl; and
(c) reacting LM$^1$Cl and Z$^1$MgCl or Z$^2$MgCl to form LM$^1$Z$^1$ or LM$^1$Z$^2$, wherein Z$^1$ or Z$^2$ represent a group.

One embodiment of the method comprises the steps of:
(a) reacting bis(2-diphenylphosphinophenyl)amine (H[PNP]) and n-butyllithium to form [PNP]Li(THF)$_2$ in the presence of THF;
(b) reacting [PNP]Li(THF)$_2$ and NiCl$_2$(DME) to form [PNP]NiCl; and
(c) reacting [PNP]NiCl and Z$^1$MgCl or Z$^2$MgCl to form [PNP]NiZ$^1$ or [PNP]NiZ$^2$, wherein Z$^1$ or Z$^2$ represent a group; and preferably, Z$^1$ or Z$^2$ is selected from the group consisting of an unsubstituted or substituted hydrocarbon group, unsubstituted or substituted aromatic group, halogen group and ligand L; more preferably, Z$^1$ or Z$^2$ represents methyl, ethyl, n-butyl, i-butyl, CH$_3$SiMe$_3$ or phenyl group.

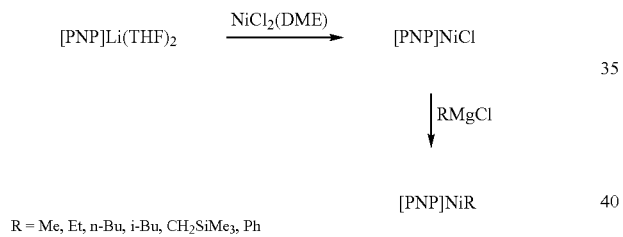

R = Me, Et, n-Bu, i-Bu, CH$_2$SiMe$_3$, Ph

A fourth method for synthesizing the complex according to the invention comprises the steps of:
(a) reacting the ligand L and n-butyllithium to form LLi(THF)$_2$ in the presence of THF;
(b) reacting LLi(THF)$_2$ and M$^1$Cl$_3$ in the presence of toluene to form LM$^1$Cl$_2$; and
(c) reacting LM$^1$Cl$_2$ and LiZ$^1$ or LiZ$^2$ to form the complex, wherein Z$^1$ or Z$^2$ represent a group.

In one embodiment of the invention, the method for the synthesis of the complex represented by formula Vd is depicted below:

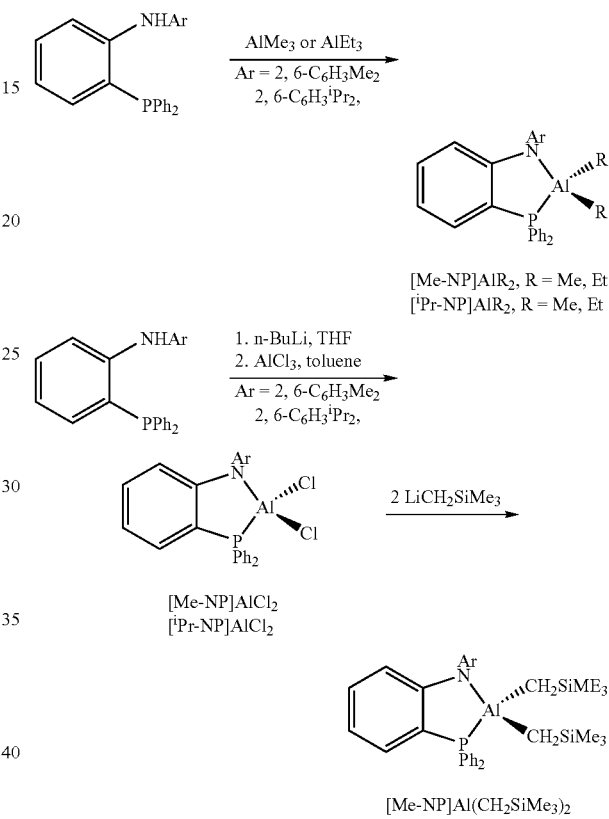

In another embodiment of the invention, the method for the synthesis of the complex represented by formula Vd is depicted below:

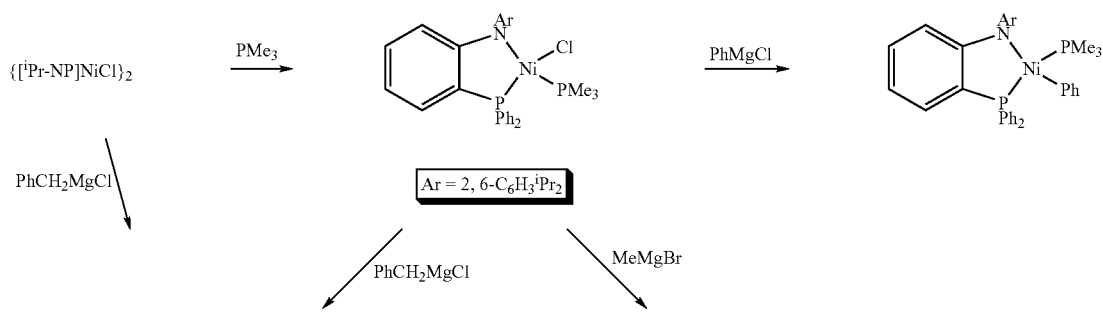

-continued

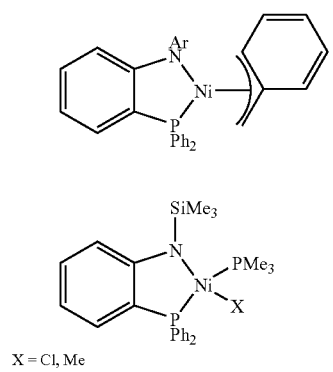

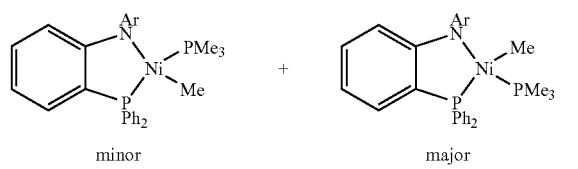

(3)

(4)

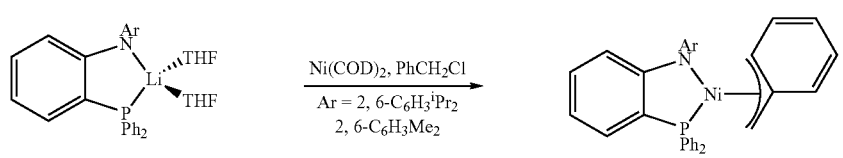

The complex comprising the ligand L of the invention is used for catalyzing carbon-carbon bond formation.

In one embodiment of the invention, the carbon-carbon bond formation comprises cross-coupling:

scheme IX

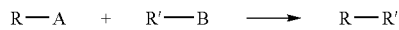

wherein:
R and R' independently represent saturated or unsaturated hydrocarbon or aromatic groups; and
A and B independently represent a group.

In one embodiment of the invention, the carbon-carbon bond formation comprises Kumada coupling reaction which is the reaction of $R^3Hal^1$ and $R^4MgHal^2$ to form $R^3$-$R^4$ bond:

Scheme XI

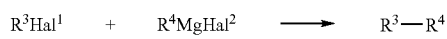

wherein:
$R^3$ and $R^4$ independently represent hydrocarbon group or aromatic group; and
$Hal^1$ and $Hal^2$ independently represent halogen atom.

One example of Kumada coupling reaction is depicted below:

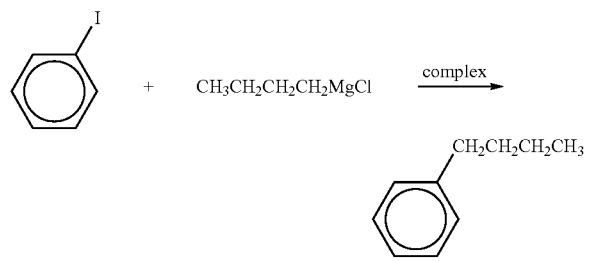

The catalyst used is the complex represented by formula VIb.

In another embodiment of the invention, the carbon-carbon bond formation comprises ethylene oligomerization which involves reacting ethyne to form 6 to 24 carbon alkenes. Preferably, the catalyst used is the complex represented by formula VIc.

In still another embodiment of the invention, the carbon-carbon bond formation comprises Heck reaction which comprises reacting $Ar^4Hal^3$ and alkene represented by the following formula VII to form aromatic alkene represented by the following formula VIII:

Scheme II

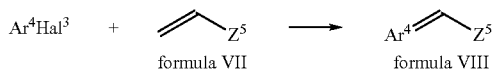

wherein:
$Ar^4$ represents aromatic group; and preferably phenyl group;
$Hal^3$ represents halogen group; and preferably I; and
$Z^5$ represents a group; and preferably phenyl group.

One example of Heck coupling reaction is depicted below:

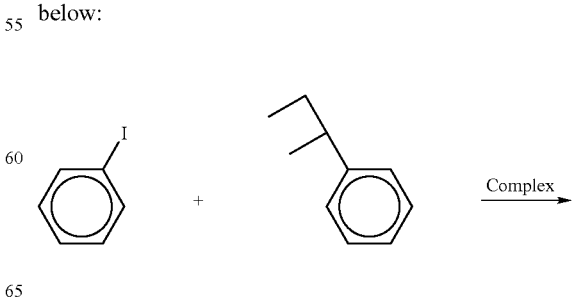

-continued

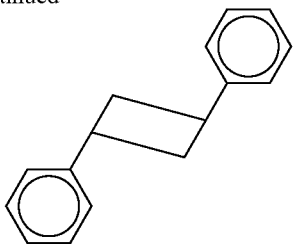

The catalyst used is the complex represented by formula VIc.

Another example of Heck coupling reaction comprises coupling aryl halides with styrene:

scheme III

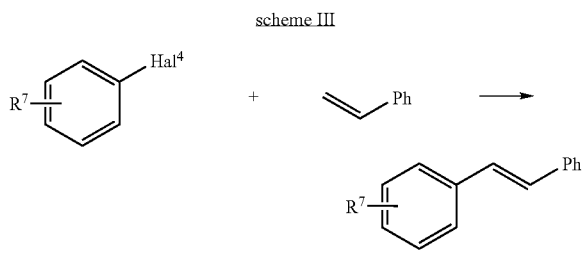

wherein:
R[7] represents H, $NO_2$, CHO, $C(O)R^1$, halogen, $OR^1$, or $NR^1$;
Hal[4] represents halogen; and
R[1] represents saturated or unsaturated hydrocarbon group with or without substituents or saturated or unsaturated aromatic group with or without substituents.

In still another embodiment of the invention, the carbon-carbon bond formation comprises Suzuki coupling reaction which comprises coupling aryl halides with styrene:

scheme X

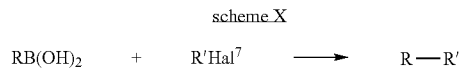

wherein Hal[7] represents halogen.

In still another embodiment of the invention, the carbon-carbon bond formation comprises ring-open polymerization:

scheme XII

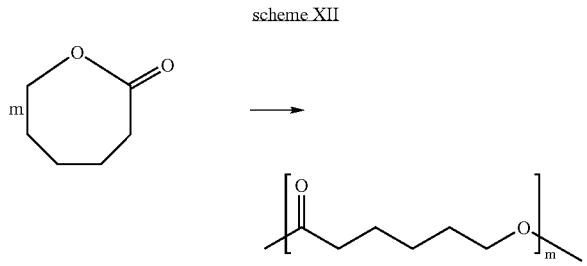

wherein m represents an integer larger than or equal to 1.

The following examples are given for the purpose of illustration only but not intended to limit the scope of the present invention.

EXAMPLE 1

Synthesis of $[NP]_2Zn$

General Procedures. Unless otherwise specified, all experiments were performed under nitrogen using standard Schlenk or glovebox techniques. All solvents were reagent grade or better and purified by standard methods. All other chemicals were used as received from commercial vendors. The NMR spectra were recorded on Varian instruments. Chemical shifts (δ) are listed as parts per million downfield from tetramethylsilane and coupling constants (J) are in hertz. $^1$H NMR spectra are referenced using the residual solvent peak at δ 7.16 for $C_6D_6$, and δ7.27 for $CDCl_3$. $^{13}$C NMR spectra are referenced using the residual solvent peak at δ 128.39 for $C_6D_6$, and δ 77.23 for $CDCl_3$. The assignment of the carbon atoms for all new compounds is based on the DEPT $^{13}$C NMR spectroscopy. $^{19}$F, $^{31}$P and $^7$Li NMR spectra are referenced externally using $CFCl_3$ in $CHCl_3$ at δ0, 85% $H_3PO_4$ at δ 0, and LiCl in $D_2O$ at δ 0, respectively. Routine coupling constants are not listed. All NMR spectra were recorded at room temperature in specified solvents. Elemental analysis was performed on a Heraeus CHN—O Rapid analyzer.

X-ray crystallography. Data for compounds H[NP], [NP]ZnEt, and $[NP]_2Zn$ were collected on a Bruker SMART 1000 CCD diffractometer with graphite monochromated Mo—Kα radiation (λ=0.7107 Å). Structures were solved by direct methods and refined by full matrix least squares procedures against $F^2$ using SHELXTL. All full-weight non-hydrogen atoms were refined anisotropically. Hydrogen atoms were placed in calculated positions. In $[NP]_2Zn$, the solvent molecule (diethyl ether) is disordered and cannot be resolved properly.

Synthesis of N-(2-fluorophenyl)-2,6-diisopropylaniline. A Schlenk flask was charged with 1-bromo-2-fluorobenzene (5.47 mL, 50.0 mmol), 2,6-diisopropylaniline (9.43 mL, 50 mmol), $Pd(OAc)_2$ (56 mg, 0.25 mmol, 0.5% equiv), bis[2-(diphenylphosphino)phenyl]ether (DPEphos, 200 mg, 0.375 mmol, 0.75% equiv), sodium tert-butoxide (6.70 g, 70 mmol, 1.4 equiv), and toluene (15 mL) under nitrogen. The flask was sealed with a rubber septum and heated to 95° C. with stirring for 5 d. Toluene was removed in vacuo and the reaction was quenched with deionized water (75 mL). The product was extracted with $CH_2Cl_2$ (75 mL) and the organic portion was separated from the aqueous layer, which was further extracted with $CH_2Cl_2$ (20 mL×2). The combined organic solution was dried over $MgSO_4$ and filtered. All volatiles were removed in vacuo to yield an orange viscous oil, which was subjected to flash column chromatography on silica gel (9:1 Hexanes/$Et_2O$). The first band (pale yellow) was collected. Solvents were removed in vacuo to give pale yellow oil; yield 12.65 g (93%). $^1$H NMR ($CDCl_3$, 200 MHz) δ 7.24-7.35 (m, 3, Ar), 7.05 (m, 1, Ar), 6.85 (t, 1, Ar), 6.65 (m, 1, Ar), 6.22 (t, 1, Ar), 5.34 (br s, 1, NH), 3.21 (septet, 2, $CHMe_2$), 1.17 (d, 12, $CHMe_2$). $^{19}$F NMR ($CDCl_3$, 470.5 MHz) δ–138.32. $^{13}$C NMR ($CDCl_3$, 125.5 MHz) δ 151.02 ($J_{CF}$=237.0, CF), 147.73, 136.41 ($J_{CF}$=10.89), 134.12, 127.59 (CH), 124.40 ($J_{CF}$=3.64, CH), 123.89 (CH), 116.99 ($J_{CF}$=7.27, CH), 114.56 ($J_{CF}$=18.20, CH), 113.11 ($J_{CF}$=2.64, CH), 28.19 ($CHMe_2$), 23.84 ($CHMe_2$). Anal. Calcd. for $C_{18}H_{22}FN$: C, 79.67; H, 8.17; N, 5.16. Found: C, 79.42; H, 8.20; N, 5.17.

Synthesis of N-(2-diphenylphosphinophenyl)-2,6-diisopropylaniline, H[NP]. A 250-mL Schlenk flask equipped with a condenser was flashed with nitrogen thoroughly. To this flask was added $KPPh_2$ (73 mL, 0.5 M in THF solution, Aldrich, 36.9 mmol). THF was removed in vacuo and a solution of N-(2-fluorophenyl)-2,6-diisopropylaniline (10 g, 36.9 mmol) in 1,4-dioxane (40 mL) was added with a syringe. The transparent, ruby reaction solution was heated to reflux for 5 d, during which time the reaction condition was monitored by $^{31}$P {$^1$H} NMR spectroscopy. All volatiles were removed from the resulting orange solution under reduced pressure and degassed deionized water (100 mL) was added. The product was extracted with deoxygenated dichloromethane (100 mL). The dichloromethane solution was separated from the aqueous layer, from which the product was further extracted with dichloromethane (20 mL×2). The combined organic solution was dried over MgSO$_4$ and filtered. All volatiles were removed in vacuo to yield the product as pale yellow oil. The product was purified by washing it with boiling EtOH (10 mL×4) until it became white powder; yield 15.2 g (94%). $^1$H NMR (CDCl$_3$, 200 MHz) δ 7.39 (m, 10, PC6H5), 7.0-7.22 (m, 4, Ar), 6.82 (m, 1, Ar), 6.65 (t, 1, Ar), 6.15 (m, 1, Ar), 5.95 (d, 1, $J_{HP}$=8, NH), 2.90 (septet, 2, CHMe$_2$), 1.06 (d, 6, CHMe$_2$), 0.94 (d, 6, CHMe$_2$). $^1$H NMR (C$_6$D$_6$, 200 MHz) δ 7.48 (m, 4, Ar), 6.60-7.15 (m, 10, Ar), 6.92 (m, 1, Ar), 6.59 (t, 1, Ar), 6.34 (m, 1, Ar), 6.26 (d, 1, $J_{HP}$=8, NH), 3.13 (septet, 2, CHMe$_2$), 1.09 (d, 6, CHMe$_2$), 0.97 (d, 6, CHMe$_2$). $^{31}$P{$^1$H} NMR (C$_6$D$_6$, 202 MHz) δ −20.11. $^{31}$P{$^1$H} NMR (Et$_2$O, 121.5 MHz) δ −19.87. $^{31}$P{$^1$H} NMR (CDCl$_3$, 121.5 MHz) δ −20.17. 13C NMR (CDCl$_3$, 75.3 MHz) δ 150.57 (J=17.1), 147.41, 135.35, 135.26, 135.24, 133.93 ($J_{CP}$=19.6), 130.28, 128.92, 128.47 ($J_{CP}$=7.5), 127.14, 123.70, 118.71, 117.63, 111.60, 28.18 (CHMe$_2$), 24.40 (CHMe$_2$), 23.03 (CHMe$_2$). Anal. Calcd. for C$_{30}$H$_{32}$NP: C, 82.35; H, 7.37; N, 3.20. Found: C, 82.32; H, 7.36; N, 3.28.

Synthesis of [NP]ZnMe. Solid N-(2-diphenylphosphinophenyl)-2,6-diisopropylaniline (218.8 mg, 0.5 mmol) was dissolved in diethyl ether (5 mL) and cooled to −35° C. To this was added a solution of ZnMe$_2$, which was prepared in situ from the reaction of ZnCl$_2$ (68.1 mg, 0.5 mmol) and MeMgCl (0.33 mL, 3 M in THF solution, Aldrich, 1 mmol) in diethyl ether at −35° C. The reaction solution was naturally warmed to room temperature and stirred for 2 d. After being filtered through a pad of Celite, the solution was concentrated to ca. 1 mL and cooled to −35° C. to afford pale yellow crystals, which were isolated from the orange solution and dried in vacuo; yield 248 mg (96%). $^1$H NMR (C$_6$D$_6$, 500 MHz) δ 7.38 (m, 4, Ar), 7.24-7.28 (m, 2, Ar), 6.95-7.08 (m, 9, Ar), 6.38 (t, 1, Ar), 6.26 (t, 1, Ar), 3.40 (septet, 2, CHMe$_2$), 1.17 (d, 6, CHMe$_2$), 1.11 (d, 6, CHMe$_2$), −0.13 (br s, 3, ZnCH$_3$). $^{31}$P{$^1$H} NMR (C$_6$D$_6$, 202.5 MHz) δ −27.34. $^{13}$C NMR (C$_6$D$_6$, 125.5 MHz) δ 163.13 ($J_{CP}$=17.32), 147.99, 146.08, 134.71 (CH), 134.11 ($J_{CP}$=14.43, CH), 133.99 (CH), 130.71 (CH), 129.57 ($J_{CP}$=10.04, CH), 129.31 ($J_{CP}$=7.28, CH), 125.54 (CH), 124.66 (CH), 114.46, 110.42, 110.10, 28.61 (CHMe$_2$), 25.21 (CHMe$_2$), 24.44 (CHMe$_2$), −12.79 (br s, ZnCH$_3$). Anal. Calcd. for C$_{31}$H$_{34}$NPZn: C, 72.02; H, 6.63; N, 2.71. Found: C, 72.36; H, 6.73; N, 2.755.

Synthesis of [NP]ZnEt. Solid N-(2-diphenylphosphinophenyl)-2,6-diisopropylaniline (200 mg, 0.457 mmol) was dissolved in diethyl ether (5 mL) and cooled to −35° C. To this was added a solution of ZnEt$_2$ (0.457 mL, 1.0 M in hexane, Aldrich, 0.457 mmol). The reaction solution was naturally warmed to room temperature and stirred for 2 d. After being filtered through a pad of Celite, the solution was evaporated to dryness, affording the desired product as a pale yellow solid which is pure by $^1$H and $^{31}$P{$^1$H} NMR spectroscopy; yield 241 mg (99%). Recrystallization of the solid from diethyl ether at −35° C. afforded colorless, X-ray quality crystals; yield 168 mg (69%). $^1$H NMR (C$_6$D$_6$, 500 MHz) δ 7.26-7.30 (m, 4, Ar), 7.12-7.17 (m, 3, Ar), 6.86-6.95 (m, 8, Ar), 6.29 (t, 1, Ar), 6.16 (t, 1, Ar), 3.29 (septet, 2, CHMe$_2$), 1.30 (t, 3, ZnCH$_2$CH$_3$), 1.07 (d, 6, CHMe$_2$), 1.02 (d, 6, CHMe$_2$), 0.69 (q, 2, ZnCH$_2$). $^{31}$P{$^1$H} NMR (C$_6$D$_6$, 202.5 MHz) δ−27.15. $^{13}$C NMR (C$_6$D$_6$, 125.5 MHz) δ 162.73 ($J_{CP}$=18.32), 145.94, 134.87 (CH), 134.05 ($J_{CP}$=14.68, CH), 130.80 (CH), 130.58, 129.64 ($J_{CP}$=10.04, CH), 128.99 ($J_{CP}$=7.27, CH), 125.72 (CH), 124.57 (CH), 114.77 ($J_{CP}$=5.52, CH), 114.12 ($J_{CP}$=5.52, CH), 110.25, 109.92, 28.73 (CHMe$_2$), 25.12 (CHMe$_2$), 24.26 (CHMe$_2$), 13.10 (ZnCH$_2$CH$_3$), 1.82 ($2J_{CP}$=35.64, ZnCH$_2$). Anal. Calcd. for C$_{32}$H$_{36}$NPZn: C, 72.38; H, 6.83; N, 2.64. Found: C, 69.62; H, 6.64; N, 2.61.

Synthesis of lithium N-(2-diphenylphosphinophenyl)-2,6-diisopropylanilide, [NP]Li(THF)$_2$. To a solution of N-(2-diphenylphosphinophenyl)-2,6-diisopropylaniline (3.085 g, 7.05 mmol) in THF (40 mL) at −35° C. was added n-BuLi (4.406 mL, 7.05 mmol, 1 equiv). The reaction mixture was naturally warmed to room temperature and stirred for 3 h. All volatiles were removed in vacuo. The red viscous residue was triturated with pentane (5 mL) to yield a yellow solid. The yellow solid was isolated from the orange solution, washed with pentane (3 mL×2), and dried in vacuo; yield 3.73 g (90%). Recrystallization of the yellow solid from a mixture of ether and pentane solution at −35° C. gave yellow crystals. $^1$H NMR (C$_6$D$_6$, 500 MHz) δ7.55 (m, 4, Ar), 7.28 (d, 2, Ar), 7.05-7.18 (m, 9, Ar), 6.32 (t, 1, Ar), 6.20 (t, 1, Ar), 3.43 (septet, 2, CHMe$_2$), 3.34 (s, 8, OCH$_2$CH$_2$), 1.31 (d, 6, CHMe$_2$), 1.22 (m, 8, OCH$_2$CH$_2$), 0.99 (d, 6, CHMe$_2$). $^7$Li{$^1$H} NMR (C$_6$D$_6$, 194 MHz) δ 1.37 (d, $^1J_{LiP}$=38). $^{31}$P{$^1$H} NMR (C$_6$D$_6$, 202 MHz) δ−11.99 (1:1:1:1 q, $^1J_{LiP}$=38). $^{13}$C NMR (C$_6$D$_6$, 125.5 MHz) δ 165.39 ($J_{CP}$=21.25), 152.23 ($J_{CP}$=3.63), 145.10, 138.45 ($J_{CP}$=7.25), 135.29, 134.41 ($J_{CP}$=17.13, CH), 132.43 (CH), 128.95 (CH), 128.87 ($J_{CP}$=7.13, CH), 124.04 (CH), 122.04 (CH), 114.02 ($J_{CP}$=4.5, CH), 113.74 ($J_{CP}$=2.63, CH), 109.94 (CH), 68.76 (OCH$_2$CH$_2$), 28.08 (CHMe$_2$), 25.68 (OCH$_2$CH$_2$), 25.66 (CHMe$_2$), 24.86 (CHMe$_2$).

Synthesis of [NP]$_2$Zn. Anhydrous ZnCl$_2$ (50 mg, 0.3653 mmol) was suspended in diethyl ether (5 mL) and cooled to −35° C. A solution of [NP]Li(THF)$_2$ (0.4289 mg, 0.7306 mmol, 2 equiv) in diethyl ether (10 mL) at −35° C. was added dropwise. The reaction mixture was stirred at room temperature overnight and passed through a pad of Celite to remove insoluble materials. The ether solution was concentrated in vacuo to ~3 mL and cooled to −35° C. to afford pale yellow crystals; yield 137.7 mg (40%). Analogous condition was employed for the 1:1 reaction, affording crystals of [NP]$_2$Zn in 38% yield. $^1$H NMR (C$_6$D$_6$, 500 MHz) δ 7.30 (m, 2, Ar), 7.08 (m, 10, Ar), 7.04 (m, 2, Ar), 6.89 (m, 4, Ar), 6.76 (m, 6, Ar), 6.41 (t, 2, Ar), 6.29 (m, 4, Ar), 6.17 (m, 4, Ar), 4.22 (septet, 2, CHMe$_2$), 3.18 (septet, 2, CHMe$_2$), 1.43 (d, 6, CHMe$_2$), 1.18 (d, 6, CHMe$_2$), 0.81 (d, 6, CHMe$_2$), 0.16 (d, 6, CHMe$_2$). $^{13}$C NMR (C$_6$D$_6$, 125.679 MHz) δ 164.71, 148.14, 147.98, 146.97, 133.75 (CH), 131.95, 130.91 (CH), 130.64, 128.08 (CH), 126.02 (CH), 2125.51 (CH), 124.67 (CH), 118.97 (CH), 116.62 (CH), 114.35 (CH), 110.85 (CH), 28.19 (CHMe), 28.20 (CHMe), 26.92 (CHMe), 24.90 (CHMe), 24.44 (CHMe), 23.75 (CHMe). $^{31}$P{$^1$H} NMR (C$_6$D$_6$, 202.5 MHz) δ−22.93. Satisfactory analysis was hampered due to the extreme air- and moisture-sensitivity of this compound.

EXAMPLE 2

Synthesis of [PNP]NiZ

General Procedures. Unless otherwise specified, all experiments were performed under nitrogen using standard Schlenk or glovebox techniques. All solvents were reagent grade or better and purified by standard methods. All other chemicals were used as received from commercial vendors. The NMR spectra were recorded on Varian instruments. Chemical shifts (δ) are listed as parts per million downfield from tetramethylsilane and coupling constants (J) are in hertz. $^1$H NMR spectra are referenced using the residual solvent peak at a 7.16 for $C_6D_6$, and δ 57.27 for $CDCl_3$. $^{13}$C NMR spectra are referenced using the residual solvent peak at δ 128.39 for $C_6D_6$, and δ 77.23 for $CDCl_3$. The assignment of the carbon atoms for all new compounds is based on the DEPT $^{13}$C NMR spectroscopy. $^{19}$F, $^{31}$P and $^7$Li NMR spectra are referenced externally using $CFCl_3$ in $CHCl_3$ at δ0, 85% $H_3PO_4$ at 60, and LiCl in $D_2O$ at δ 0, respectively. Routine coupling constants are not listed. All NMR spectra were recorded at room temperature in specified solvents. Mass spectra were recorded on a Finnigan MAT 95XL Mass Spectrometer. Elemental analysis was performed on a Heraeus CHN—O Rapid analyzer. For some hydrocarbyl derivatives, the carbon analyses were reproducibly lower by ca. 1-2% than the expected values after several attempts, due likely to formation of carbides upon combustion of these compounds.

X-ray crystallography. Data for compounds H[PNP] and [PNP]Li(THF)$_2$ were collected on a Bruker SMART 1000 CCD diffractometer with graphite monochromated Mo—Kα radiation (λ=0.7107 Å). Structures were solved by direct methods and refined by full matrix least squares procedures against $F^2$ using SHELXTL. All full-weight non-hydrogen atoms were refined anisotropically. Hydrogen atoms were placed in calculated positions.

Synthesis of di(2-fluorophenyl)amine. A Schlenk flask was charged with 2-fluoroaniline (5.55 g, 50 mmol), 1-bromo-2-fluorobenzene (8.75 g, 50 mmol), Pd(OAc)$_2$ (0.020 g, 0.089 mmol, 0.5% equiv), DPEPhos (0.216 g, 0.401 mmol, 0.75% equiv), NaO$^t$Bu (7.185 g, 74.84 mmol, 1.4 equiv), and toluene (45 mL) under nitrogen. The reaction mixture was heated to reflux with stirring. The reaction was monitored by GC, which showed complete formation of the desired product in 1 d. After being cooled to room temperature, the reaction was quenched with deionized water (45 mL). The organic portion was separated from the aqueous layer, which was further extracted with toluene (10 mL×2). The combined organic solution was dried over MgSO$_4$ and filtered. All volatiles were removed in vacuo to yield red oil, which was directly used for the subsequent reaction; yield 9.38 g (91.4%). $^1$H NMR (CDCl$_3$, 500 MHz) δ 7.42 (m, 2, Ar), 7.25 (m, 2, Ar), 7.20 (m, 2, Ar), 7.04 (m, 2, Ar), 6.03 (br s, 1, NH). $^{19}$F NMR (CDCl$_3$, 470.5 MHz) δ−133.07. $^{13}$C NMR (CDCl$_3$, 125 MHz) δ 153.45 ($J_{CF}$=241, CF), 130.45 ($J_{CF}$=11.75, CN), 124.14 ($J_{CF}$=3.63, CH), 121.38 ($J_{CF}$=7.25, CH), 117.98 (CH), 115.45 ($J_{CF}$=19.00, CH). LR-MS (EI): calcd. for $C_{12}H_9F_2N$ m/z 205, found m/z 205. Anal. Calcd. for $C_{12}H_9F_2N$: C, 70.24; H, 4.42; N, 6.83. Found: C, 70.13; H, 4.52; N, 6.69.

Synthesis of bis(2-diphenylphosphinophenyl)amine (H[PNP]). A 100-mL Schlenk flask equipped with a condenser was flashed with nitrogen thoroughly. To this flask was added KPPh$_2$ (20 mL, 0.5 M in THF solution, Aldrich, 10 mmol). THF was removed in vacuo and a solution of di(2-fluorophenyl)amine (1.00 g, 4.88 mmol) in 1,4-dioxane (8 ml) was added with a syringe. The transparent, ruby reaction solution was heated to reflux with stirring. The reaction condition was monitored by $^{31}$P{$^1$H} NMR spectroscopy, which revealed the completion of reaction in 2 d. The resulting yellow solution was evaporated to dryness in vacuo. The residue was treated with degassed deionized water (50 mL) and the product was extracted with deoxygenated dichloromethane (15 mL). The dichloromethane solution was separated from the aqueous layer, from which the product was further extracted with dichloromethane (15 mL×3). The combined organic solution was dried over MgSO$_4$ and filtered. All volatiles were removed in vacuo to yield the product as a pale yellow crystalline solid; yield 2.1 g (80.15%). $^1$H NMR (CDCl$_3$, 300 MHz) δ 7.10-7.23 (m, 24, Ar), 6.69-6.76 (m, 5, Ar and NH). $^{31}$P{$^1$H} NMR (CDCl$_3$, 121.5 MHz) δ−19.58. $^{31}$P{$^1$H} NMR (Et$_2$O, 121.5 MHz) δ−18.62. $^{13}$C NMR (CDCl$_3$, 75 MHz) δ 146.51 ($J_{CP}$=21.1), 135.78 ($J_{CP}$=8.0), 134.14, 133.72 ($J_{CP}$=21.1), 129.64, 128.53 ($J_{CP}$=12.0), 128.46 ($J_{CP}$=7.5), 126.34 ($J^{CP}$=10.1), 121.51, 118.16. Anal. Calcd. for $C_{36}H_{29}NP_2$: C, 80.43; H, 5.44; N, 2.61. Found: C, 80.04; H, 5.56; N, 2.69.

Synthesis of [PNP]Li(THF)$_2$. n-Butyllithium (3.35 mL, 1.6 M in hexanes, 5.36 mmol, 1.6 equiv) was added dropwise to a THF solution (20 mL) of H[PNP] (1.80 g, 3.35 mmol) at −35 C with stirring. Gas evolution was observed upon addition of the lithium reagent. The reaction solution was naturally warmed to room temperature and stirred for 2 h. All volatiles were removed in vacuo. The solid residue was triturated with pentane (5 mL×2), providing the product as a pale yellow solid which was isolated and dried in vacuo; yield 1.84 g (78.46%). Single crystals for X-ray diffraction analysis were grown from a concentrated THF solution at room temperature. $^1$H NMR ($C_6D_6$, 500 MHz) δ 7.63 (t, 2, Ar), 7.45 (m, 6, Ar), 6.97-7.17 (m, 18, Ar), 6.52 (t, 2, Ar), 3.48 (m, 8, OCH$_2$CH$_2$), 1.25 (m, 8, OCH$_2$CH$_2$). $^{31}$P{$^1$H} NMR (THF, 121.5 MHz) δ−13.68 (sharp). $^{31}$P{$^1$H} NMR ($C_6D_6$, 202 MHz) δ−14.44 (br s, 3.3 Hz peak width at half-height). $^7$Li{$^1$H} NMR ($C_6D_6$, 194.2 MHz) δ 2.42 (br s, 55.93 Hz peak width at half-height). $^{13}$C NMR (CDCl$_3$, 125.5 MHz) δ 163.26 ($J_{CP}$=19.75), 138.47 (CN), 134.84 (CH), 134.29 ($J_{CP}$=17.00, CH), 131.47 (CH), 128.87 ($J_{CP}$=6.63, CH), 128.77 (CH), 122.90 ($J_{CP}$=16.00), 117.89 (CH), 115.78 (CH), 68.70 (OCH$_2$CH$_2$), 25.88 (OCH$_2$CH$_2$).

Synthesis of [PNP]NiCl. Solid NiCl$_2$(DME) (172.7 mg, 0.785 mmol) was suspended in THF (10 mL) and cooled to −35° C. A cold solution of [PNP]Li(THF)$_2$ (540 mg, 0.785 mmol) in THF (10 mL) at −35° C. was added dropwise to the suspension to result in gradual dissolution of solid NiCl$_2$(DME), and a homogeneous dark green solution formed. The reaction mixture was stirred at room temperature for 2 h. All volatiles were removed in vacuo. The solid residue was extracted with CH$_2$Cl$_2$ (20 mL). The green CH$_2$Cl$_2$ solution was filtered through a pad of Celite and evaporated to dryness, providing the product as a green solid, yield 464 mg (93.6%). $^1$H NMR ($C_6D_6$, 500 MHz) δ 7.92-7.95 (m, 8, Ar), 7.61 (d, 2, Ar), 6.96-7.04 (m, 14, Ar), 6.83 (t, 2, Ar), 6.35 (t, 2, Ar). $^{31}$P{$^1$H} NMR ($C_6D_6$, 202 MHz) δ 18.77. $^{13}$C{$^1$H} NMR ($C_6D_6$, 125 MHz) δ 163.31 (t, $J_{CP}$=14.43), 135.15 (CH), 134.38 (t, $J_{CP}$=5.90, CH), 132.38 (CH), 130.95 (CH), 130.69 (t, $J_{CP}$=23.97), 129.29 (t, $J_{CP}$=4.89, CH), 123.65 (t, $J_{CP}$=23.47), 118.51 (t, $J_{CP}$=3.14, CH), 117.87 (t, $J_{CP}$=5.90, CH). Anal. Calcd. for $C_{36}H_{28}ClNNiP_2$: C, 68.56; H, 4.47; N, 2.22. Found: C, 68.36; H, 4.57; N, 2.18.

General procedures for the synthesis of [PNP]NiR (R=Me, Et, n-Bu, i-Bu, CH$_2$SiMe$_3$, Ph). Alkyl magnesium chloride (1 equiv) was added dropwise to a green solution of

[PNP]NiCl in THF at −35° C. Upon addition, the solution became red in color. After being stirred at room temperature for 2.5 h, the reaction solution was stripped to dryness, triturated with pentane, extracted with benzene, and passed through a pad of Celite. The solvent was removed in vacuo to afford the desired product. The hydrocarbyl compounds are typically red in color.

Synthesis of [PNP]NiMe. Yield 93%. $^1$H NMR ($C_6D_6$, 499.767 MHz) δ 7.813 (m, 2, Ar), 7.687 (m, 8, Ar), 7.109 (m, 2, Ar), 6.97 9 (m, 14, Ar), 6.425 (t, 2, Ar), 0.128 (t, 3, $^3J_{HP}$=8.5 Hz, NiCH$_3$). $^{13}$P{$^1$H} NMR ($C_6D_6$, 202.306 MHz) δ 27.605. $^{31}$P{$^1$H} NMR (THF, 121.416 MHz) δ 27.270. $^{31}$P{$^1$H} NMR (CH$_2$Cl$_2$, 121.415 MHz) δ 27.150. $^{13}$C{$^1$H} NMR ($C_6D_6$, 125.678 MHz) δ 162.746 (t, $J_{CP}$=14.1 Hz, C), 134.932 (s, CH), 134.107 (t, $J_{CP}$=5.9 Hz, CH), 132.587 (t, $J_{CP}$=21.9 Hz, C), 132.385 (s, CH), 130.416 (s, CH), 129.237 (t, $J_{CP}$=4.5 Hz, CH), 125.091 (t, $J_{CP}$=22.7 Hz, C), 117.153 (s, CH), 116.386 (s, CH), −15.365 (t, $J_{CP}$=21.9 Hz, NiCH$_3$). Anal. Calcd. for $C_{37}H_{31}NNiP_2$: C, 72.82; H, 5.12; N, 2.30. Found: C, 71.49; H, 5.39; N, 2.27.

Synthesis of [PNP]NiEt. Yield 93%. $^1$H NMR ($C_6D_6$, 499.767 MHz) δ 7.759 (m, 10, Ar), 7.175 (m, 2, Ar), 7.029 (m, 12, Ar), 6.969 (t, 2, Ar), 6.439 (t, 2, Ar), 1.074 (qt, 2, $^3J_{HP}$=2 Hz, $^3J_{HH}$=7.5 Hz, NiCH$_2$), 0.755 (t, 3, CH$_3$). $^{31}$P{$^1$H} NMR (THF, 121.416 MHz) δ 27.578. $^{31}$P{$^1$H} NMR ($C_6D_6$, 202.310 MHz) δ 26.418. $^{13}$C{$^1$H} NMR ($C_6D_6$, 125.678 MHz) δ 162.554 (t, $J_{CP}$=13.64 Hz, C), 134.476 (s, CH), 134.144 (t, $J_{CP}$=6.35 Hz, CH), 132.750 (t, $J_{CP}$=21.37 Hz, C), 132.288 (s, CH), 130.397 (s, CH), 129.191 (t, $J_{CP}$=4.52 Hz, CH), 125.509 (t, $J_{CP}$=22.62 Hz, C), 117.026 (t, $J_{CP}$=3.64 Hz, CH), 116.362 (t, $J_{CP}$=4.59 Hz, CH), 15.357 (t, $^3J_{CP}$=2.7 Hz, CH$_3$), −2.800 (t, $^2J_{CP}$=19.48 Hz, NiCH$_2$). Anal. Calcd. for $C_{38}H_{33}NNiP_2$: C, 73.11; H, 5.33; N, 2.24. Found: C, 70.85; H, 5.33; N, 2.25.

Synthesis of [PNP]Ni(n-Bu). Yield 100%. $^1$H NMR ($C_6D_6$, 499.767 MHz) δ 7.782 (m, 10, Ar), 7.202 (dt, 2, Ar), 7.036 (m, 12, Ar), 6.969 (t, 2, Ar), 6.446 (t, 2, Ar), 1.090 (m, 2, NiCH$_2$), 0.980 (m, 4, NiCH$_2$(CH$_2$)$_2$CH$_3$), 0.587 (t, 3, CH$_3$). $^{31}$P{$^1$H} NMR (THF, 121.416 MHz) δ 26.79. $^{31}$P{$^1$H} NMR ($C_6D_6$, 202.306 MHz) δ 27.056. $^{13}$C{$^1$H} NMR ($C_6D_6$, 125.678 MHz) δ 162.576 (t, $J_{CP}$=13.57 Hz, C), 134.419 (s, CH), 134.144 (t, $J_{CP}$=6.35 Hz, CH), 132.816 (t, $J_{CP}$=21.3 Hz, C), 132.303 (s, CH), 130.412 (s, CH), 129.141 (t, $J_{CP}$=4.96 Hz, CH), 125.524 (t, $J_{CP}$=23.19 Hz, C), 117.019 (t, $J_{CP}$=3.14 Hz, CH), 116.377 (t, $J_{CP}$=5.03 Hz, CH), 33.285 (s, CH$_2$), 28.216 (s, CH$_2$), 14.289 (s, CH$_3$), 5.243 (t, $J_{CP}$=19.10 Hz, NiCH$_2$).

Synthesis of [PNP]Ni(i-Bu). Yield 76%. $^1$H NMR ($C_6D_6$, 499.767 MHz) δ 7.796 (m, 8, Ar), 7.701 (m, 2, Ar), 7.143 (m, 2, Ar), 7.033 (m, 12, Ar), 6.951 (t, 2, Ar), 6.424 (t, 2, Ar), 1.677 (m, 1, CH), 1.019 (q, 2, J=7.5 Hz, NiCH$_2$), 0.749 (d, 6, CH$_3$). $^{31}$P{$^1$H} NMR (THF, 121.416 MHz) δ 27.578. $^{31}$P{$^1$H} NMR ($C_6D_6$, 202.310 MHz) 526.795. $^{13}$C{$^1$H} NMR ($C_6D_6$, 125.679 MHz) δ 162.438 (t, $J_{CP}$=13.13 Hz, C), 134.303 (s, CH), 134.122 (t, $J_{CP}$=6.35 Hz, CH), 132.989 (t, $J_{CP}$=21.3 Hz, C), 132.318 (s, CH), 130.469 (s, CH), 129.141 (t, $J_{CP}$=4.52 Hz, CH), 125.914 (t, $J_{CP}$=23.12 Hz, C), 117.033 (s, CH), 116.304 (s, CH), 34.266 (s, NiCH$_2$CHMe$_2$), 27.703 (s, NiCH$_2$CHMe$_2$), 18.527 (t, $^3J_{CP}$=19.54 Hz, NiCH$_2$CHMe$_2$).

Synthesis of [PNP]NiCH$_2$SiMe$_3$. Yield 100%. $^1$H NMR ($C_6D_6$, 500 MHz) δ 7.83-7.87 (m, 8, Ar), 7.70 (d, 2, Ar), 7.23 (m, 2, Ar), 7.03 (m, 12, Ar), 6.94 (t, 2, Ar), 6.46 (t, 2, Ar), −0.08 (t, 2, $^3J_{HP}$=12, NiCH$_2$), −0.17 (s, 9, Si(CH$_3$)$_3$). $^{31}$P{$^1$H} NMR ($C_6D_6$, 202 MHz) δ 23.90. $^{13}$C NMR ($C_6D_6$, 125 MHz) δ 162.27 (t, $J_{CP}$=14.55, C), 134.47 (t, $J_{CP}$=5.5, CH), 134.03 (CH), 132.94 (t, $J_{CP}$=20.96, C), 132.15 (CH), 130.50 (CH), 129.12 (t, $J_{CP}$=4.52, CH), 125.71 (t, $J_{CP}$=22.84), 117.19 (CH), 116.81 (t, $J_{CP}$=4.52, CH), 3.55 (SiCH$_3$), −12.97 (t, $^2J_{CP}$=18.83, NiCH$_2$). Anal. Calcd. for $C_{40}H_{39}NNiP_2Si$: C, 70.40; H, 5.76; N, 2.05. Found: C, 70.09; H, 5.79; N, 2.10.

Synthesis of [PNP]NiPh. Yield 97%. $^1$H NMR ($C_6D_6$, 499.767 MHz) δ 7.935 (dt, 2, Ar), 7.486 (m, 8, Ar), 7.173 (m, 2, Ar), 7.119 (m, 2, Ar), 7.036 (m, 2, Ar), 7.463 (m, 12, Ar), 6.726 (t, 2, Ar), 6.667 (m, 1, Ar), 6.457 (t, 2, Ar). $^{31}$P{$^1$H} NMR ($C_6D_6$, 202.310 MHz) 524.446. $^{13}$C{$^1$H} NMR ($C_6D_6$, 125.679 MHz) δ 163.086 (t, $J_{CP}$=14.1 Hz, C), 150.966 (t, $^2J_{CP}$=28.2 Hz, NiC), 138.542 (t, $J_{CP}$=3.6 Hz, CH), 135.351 (s, CH), 133.983 (t, $J_{CP}$=3 Hz, CH), 132.435 (s, CH), 131.299 (t, $J_{CP}$=23.6 Hz, C), 129.389 (s, CH), 128.969 (t, $J_{CP}$=5 Hz, CH), 126.328 (s, CH), 124.758 (t, $J_{CP}$=22.2 Hz, C), 121.849 (s, CH), 117.493 (s, CH), 116.697 (t, $J_{CP}$=5 Hz, CH).

EXAMPLE 3

Synthesis of [MeNP]NiZ or [$^i$Pr-NP]NiZ

General Procedures. Unless otherwise specified, all experiments were performed under nitrogen using standard Schlenk or glovebox techniques. All solvents were reagent grade or better and purified by standard methods. The NMR spectra were recorded on Varian instruments. Chemical shifts (δ) are listed as parts per million downfield from tetramethylsilane, and coupling constants (J) and peak widths at halfheight (Δν$_{1/2}$) Δare in hertz. $^1$H NMR spectra are referenced using the residual solvent peak at δ 7.16 for $C_6D_6$ and δ 2.09 for toluene-d8 (the most upfield resonance). $^{13}$C NMR spectra are referenced using the residual solvent peak at δ 128.39 for $C_6D_6$. The assignment of the carbon atoms for all new compounds is based on the DEPT $^{13}$C NMR spectroscopy. $^{31}$P and $^7$Li NMR spectra are referenced externally using 85% $H_3PO_4$ at δ 0 and LiCl in $D_2O$ at δ 0, respectively. Routine coupling constants are not listed. All NMR spectra were recorded at room temperature in specified solvents unless otherwise noted. Elemental analysis was performed on a Heraeus CHN—O Rapid analyzer.

Materials. Compounds N-(2-diphenylphosphinophenyl)-2,6-diisopropylaniline (H[$^i$Pr-NP]), N-(2-diphenylphosphinophenyl)-2,6-dimethylaniline (H[Me-NP]), and [iPr-NP]Li (THF)$_2$ were prepared according to the procedures reported previously. All other chemicals were obtained from commercial vendors and used as received.

X-ray Crystallography. Data for compounds H[$^i$Pr-NP] and [Me-NP]Li(THF)$_2$ were collected on a Bruker SMART 1000 CCD diffractometer with graphite-monochromated Mo Kα radiation (λ=0.7107 Å). Structures were solved by direct methods and refined by full matrix least squares procedures against F$^2$ using SHELXTL. All full-weight non-hydrogen atoms were refined anisotropically. Hydrogen atoms were placed in calculated positions. Data for compounds [$^i$Pr-NP]NiCl(PMe$_3$), [$^i$Pr-NP]NiMe(PMe$_3$), [$^i$Pr-NP]NiPh(PMe$_3$), [$^i$Pr-NP]Ni(η$_3$—CH$_2$Ph), and [Me-NP]Ni-(η$_3$-CH$_2$Ph) were collected on a Bruker-Nonius Kappa CCD diffractometer with graphite-monochromated Mo Kα radiation (λ=0.7107 Å). Structures were solved by direct methods and refined by full matrix least squares procedures against F$^2$ using the maXus or WinGX crystallographic software package. All full-weight non-hydrogen atoms were refined anisotropically. Hydrogen atoms were placed in calculated positions.

Synthesis of [Me-NP]Li(THF)$_2$. To a solution of H[Me-NP] (2.0 g, 5.24 mmol) in THF (15 mL) at −35° C. was added n-BuLi (3.3 mL, 5.24 mmol, 1 equiv). The reaction mixture was naturally warmed to room temperature and stirred for 3 h. All volatiles were removed in vacuo. The red viscous residue was triturated with pentane (15 mL) to yield a yellow solid. The yellow solid was isolated from the orange solution, washed with pentane (5 mL_3), and dried in vacuo; yield 2.67 g (99%). Recrystallization of the yellow solid from a concentrated diethyl ether solution at −35° C. gave yellow crystals suitable for X-ray crystallography. $^1$H NMR ($C_6D_6$, 500 MHz): δ 7.58 (m, 4, Ar), 7.23 (d, 2, Ar), 7.07-7.16 (m, 8, Ar), 6.97 (m, 1, Ar), 6.38 (m, 1, Ar), 6.33 (m, 1, Ar), 3.23 (m, 8, $OCH_2CH_2$), 2.26 (s, 6, $CH_3$), 1.19 (m, 8, $OCH_2CH_2$). $^{31}P\{^1H\}$ NMR ($C_6D_6$, 202 MHz): δ−13.66 (br s, $\Delta\nu_{1/2}$) 75 Hz}. $^{31}P\{^1H\}$NMR (toluened8, 202 MHz): δ−12.96. $^{31}P\{^1H\}$ NMR (toluene-d8, −20° C., 202 MHz): δ− 12.72 (1:1:1:1 q, 1JLiP) 34 Hz}. $^7Li\{^1H\}$ NMR ($C_6D_6$, 194 MHz): δ 1.37 (br s, $\Delta\nu_{1/2}$) 21 Hz}. $^7Li\{^1H\}$NMR (toluene-d8, 194 MHz): 52.08. $^7Li\{^1H\}$NMR (toluene-d8, −20° C., 194 MHz): (δ 2.12 (d, 1JLiP) 34 Hz). $^{13}C$ NMR ($C_6D_6$, 125.5 MHz): δ 163.88 ($J_{CP}$) 21.63, CP), 154.81, 138.20 (PCCN), 135.69 (CH), 134.38 ($J_{CP}$) 16.25, CH), 134.06, 132.74 (CH), 129.00 (CH), 128.88 ($J_{CP}$) 6.63, CH), 128.68 (CH), 120.65 (CH), 114.00 ($J_{CP}$) 3.75 Hz), 113.01 (CH), 110.47 (CH), 68.70 ($OCH_2CH_2$), 25.61 ($OCH_2CH_2$), 19.73 ($CH_3$).

Synthesis of [$^i$Pr-NP]NiCl$_2$. Method 1: Solid NiCl$_2$-(DME) (400 mg, 1.818 mmol) was suspended in THF (60 mL) and cooled to −35° C. To this was added dropwise a solution of [$^i$Pr-NP]Li(THF)$_2$ (1.0672 g, 1.818 mmol) in THF (20 mL) at −35° C. Upon addition, the reaction mixture became red in color and the suspended NiCl$_2$(DME) dissolved. The solution was stirred at room temperature overnight. All volatiles were removed in vacuo. The resulting viscous, reddish-brown residue was dissolved in $CH_2Cl_2$ (15 mL) and passed through a pad of Celite, which was further washed with $CH_2Cl_2$ (2 mL) until the washings were colorless. The filtrate was evaporated in vacuo to dryness to give the product as a deep red solid, which was gently washed with diethyl ether (3 mL_2) and dried in vacuo; yield 780.6 mg (81%). Method 2: Solid NiCl$_2$-(DME) (100 mg, 0.454 mmol) was suspended in THF (15 mL) at room temperature. To this was added a THF solution (5 mL) of H[$^i$Pr-NP] (198.9 mg, 0.454 mmol). The reaction mixture was stirred at room temperature for 30 min, and NEt$_3$ (0.095 mL, 0.681 mmol, 1.5 equiv) was added. After being stirred for 1 h, the reaction mixture was evaporated to dryness under reduced pressure. The residue was triturated with pentane (2 mL_2). The product was extracted with $CH_2Cl_2$ (10 mL) and filtered through a pad of Celite. Solvent was removed in vacuo to afford the crude product as a brick-red solid. The product was purified by dissolving the solid in a minimal amount of THF (ca. 1 mL) followed by addition of pentane (3 mL) to induce the precipitation of a red solid. The red solid was isolated by decantation of the solution, washed with pentane, and dried in vacuo; yield 150 mg (62%). $^1$H NMR ($C_6D_6$, 500 MHz): δ 7.75 (m, 4, Ar), 7.09 (m, 3, Ar), 7.00-7.04 (m, 6, Ar), 6.79 (m, 1, Ar), 6.64 (t, 1, Ar), 6.09 (t, 1, Ar), 5.85 (d, 1, Ar), 3.94 (septet, 2, CHMe$_2$), 1.51 (d, 6, CHMe$_2$), 1.11 (d, 6, CHMe$_2$). $^{31}P\{^1H\}$NMR ($C_6D_6$, 202.5 MHz): δ 32.45 (br s, $\Delta\nu_{1/2}$) 80 Hz}. $^{31}P\{^1H\}$NMR (THF, 121.4 MHz): δ 33.06 (br s). $^{13}C$ NMR ($C_6D_6$, 125.5 MHz): δ 167.63, 147.92, 145.77, 133.88 (CH), 133.64 (CH), 132.81 (CH), 131.27 (CH), 129.92 ($J_{CP}$) 44.80), 129.26 (CH), 125.93 (CH), 124.12 (CH), 116.71 (CH), 114.05 (CH), 117.5 ($J_{CP}$) 37.65). Anal. Calcd for ($C_{30}H_{31}ClNNiP)_2$: C, 67.90; H, 5.89; N, 2.64. Found: C, 68.12; H, 6.44; N, 2.51.

Synthesis of [$^i$Pr-NP]NiCl(PMe$_3$). PMe$_3$ (0.38 mL, 1.0 M in THF, Aldrich, 0.38 mmol, 1 equiv per nickel) was added to a red solution of [$^i$Pr-NP]NiCl$_2$ (200 mg, 0.19 mmol) in THF (8 mL) at room temperature. The solution became green in color over the course of 30 min. After being stirred at room temperature overnight, the solution was evaporated to dryness under reduced pressure. The product was isolated as a green solid, which was spectroscopically pure by $^{31}P\{^1H\}$NMR spectroscopy; yield 186.8 mg (81.6%). Emerald cubic crystals of [$^i$Pr-NP]NiCl(PMe$_3$) suitable for X-ray diffraction analysis were grown by layering pentane on a concentrated THF solution at −35° C. $^1$H NMR ($C_6D_6$, 500 MHz): δ 7.81 (m, 4, Ar), 7.34 (m, 3, Ar), 7.03 (m, 2, Ar), 6.99 (m, 4, Ar), 6.79 (t, 1, Ar), 6.71 (m, 1, Ar), 6.21 (t, 1, Ar), 6.08 (m, 1, Ar), 3.94 (septet, 2, CHMe$_2$), 1.65 (d, 6, CHMe$_2$), 1.20 (d, 6, CHMe$_2$), 0.74 (d, 9, 2$J_{HP}$) 9.5, PMe$_3$}. $^{31}P\{^1H\}$NMR ($C_6D_6$, 202.5 MHz): δ 47.29 (d, 2$J_{PP}$) 88 Hz}, −16.98 (d, 2$J_{PP}$) 88 Hz}. $^{31}P\{^1H\}$ NMR (THF, 121.4 MHz): δ 46.89 (d, 2$J_{PP}$) 88 Hz}, −15.75 (d, 2$J_{PP}$) 88 Hz}. $^{13}C\{^1H\}$NMR ($C_6D_6$, 125.5 MHz): δ 146.47, 134.24, 134.12, 134.05, 131.91, 131.44, 129.37, 129.20, 125.60, 124.09, 116.20, 113.66, 29.14 (CHMe$_2$), 25.27 (CHMe$_2$), 24.97 (CHMe$_2$), 16.08 (dd, 1$J_{CP}$) 30.92, $^3J_{CP}$) 9.17, PMe$_3$). Anal. Calcd for $C_{33}H_{40}ClNNiP_2$: C, 65.32; H, 6.64; N, 2.31. Found: C, 64.72; H, 6.71; N, 2.35.

Synthesis of [$^i$Pr-NP]NiMe(PMe$_3$). Solid [$^i$Pr-NP]NiCl—(PMe$_3$) (56.7 mg, 0.094 mmol) was dissolved in THF (3 mL) and cooled to −35° C. To this was added MeMgCl (0.03 mL, 3 M in THF, Aldrich, 0.094 mmol) dropwise. The reaction mixture was naturally warmed to room temperature and stirred overnight. An aliquot was taken and examined by $^{31}P$-{$^1H$}NMR spectroscopy, which indicated complete consumption of [$^i$Pr-NP]NiCl(PMe$_3$) and exhibited two pairs of doublet resonances with the relative intensities of ca. 9:1 (2$J_{PP}$) 30 Hz for major and 2$J_{PP}$} 302 Hz for minor}. All volatiles were removed in vacuo. The red residue thus obtained was triturated with pentane (2 mL_2), extracted with benzene (6 mL), and filtered through a pad of Celite. The Celite pad was further washed with benzene (1 mL_2) until the washings became colorless. Solvent was removed in vacuo to give the product as a ruby solid. Crystals suitable for X-ray crystallography were grown by slow evaporation of a concentrated benzene solution at room temperature; yield 43.6 mg (79%). The $^1$H and $^{31}P\{^1H\}$NMR spectra of the X-ray quality crystals indicated the presence of two geometric isomers in a ratio of ca. 3:1 with the major corresponding to a cis relationship between the two phosphorus donors. Spectroscopic data for the major isomer: $^1$H NMR ($C_6D_6$, 500 MHz): δ 7.78 (m, 4, Ar), 7.40 (m, 3, Ar), 7.08 (m, 2, Ar), 7.05 (m, 4, Ar), 6.92 (dt, 1, Ar), 6.87 (dt, 1, Ar), 6.28 (t, 1, Ar), 6.12 (dd, 1, Ar), 3.90 (septet, 2, CHMe$_2$), 1.46 (d, 6, CHMe$_2$), 1.24 (d, 6, CHMe$_2$), 0.70 (d, 9, 2$J_{HP}$) 9 Hz, PMe$_3$}, −0.12 (dd, 3, 3$J_{HP}$NP) 4.0 Hz, 3$J_{HP}$ PMe$_3$} 7.5 Hz, NiMe}. $^{31}P\{^1H\}$NMR ($C_6D_6$, 202.3 MHz): δ 35.60 (d, 2$J_{PP}$) 25.49 Hz, NP}, −7.46 (d, 2$J_{PP}$) 25.49 Hz, PMe$_3$}. $^{31}P$-{$^1H$}NMR (THF, 80.953 MHz): δ 35.25 (d, 2$J_{PP}$) 29.95 Hz, NP}, −6.26 (d, 2$J_{PP}$) 29.95 Hz, PMe$_3$}. $^{13}C\{^1H\}$ NMR ($C_6D_6$, 125.678 MHz): δ δ 28.55 (s, CHMe$_2$), 25.62 (s, CHMe$_2$), 24.65 (s, CHMe$_2$), 17.03 (dd, 1$J_{CP}$) 30 Hz, 3$J_{CP}$} 5 Hz, PMe$_3$}, 11.13 (dd, 2$J_{CP}$ PMe$_3$) 38.84 Hz, 2$J_{CP}$ NP} 58.69 Hz, NiMe}. Spectroscopic data for the minor isomer: $^1$H NMR ($C_6D_6$, 500 MHz): δ δ 3.84 (septet, 2, CHMe$_2$), 1.30 (d, 6, CHMe$_2$), 1.18 (d, 6, CHMe$_2$), 0.55 (dd, 9, 2$J_{HP}$) 7 Hz, 4$J_{HP}$} 1 Hz, PMe$_3$}, −0.42 (dd, 3, 3$J_{HP}$ NP) 12 Hz, 3$J_{HP}$ PMe$_3$} 7.5 Hz, NiMe}. $^{31}P\{^1H\}$NMR ($C_6D_6$, 202.3 MHz): δ 38.95 (d, 2$J_{PP}$) 301.04 Hz, NP}, −17.96 (d, 2$J_{PP}$) 301.04 Hz, PMe$_3$}. $^{31}P\{^1H\}$NMR (THF, 80.953 MHz): δ 38.66 (d, 2$J_{PP}$) 302.3 Hz, NP}, −17.10 (d, 2$J_{PP}$) 302.3 Hz, PMe$_3$}. 13C{$^1H$} NMR ($C_6D_6$, 125.678 MHz): δ δ 28.85 (s, CHMe$_2$), 24.96 (s, CHMe$_2$), 24.21 (s, CHMe$_2$), 13.45 (d, 1J$_{CP}$) 23 Hz, PMe$_3$), NiMe not found. Anal. Calcd for C$_{34}$H$_{43}$—NNiP$_2$: C, 69.65; H, 7.39; N, 2.39. Found: C, 69.32; H, 7.35; N, 2.37.

Synthesis of [$^i$Pr-NP]NiPh(PMe$_3$). Solid [$^i$Pr-NP]NiCl—(PMe$_3$) (110 mg, 0.181 mmol) was dissolved in THF (6 mL) and cooled to −35° C. To this was added PhMgCl (0.09 mL, 2.05 M in THF, Strem, 0.181 mmol) dropwise. The reaction mixture was naturally warmed to room temperature and stirred overnight. All volatiles were removed in vacuo. The red solid residue was extracted with benzene (3 mL) and filtered through a pad of Celite, which was further washed with benzene (1 mL_2) until the washings became colorless. Solvent was removed in vacuo to give the product as a brownish red solid; yield 100.8 mg (86%). Crystals suitable for X-ray analysis were grown by layering pentane on a concentrated diethyl ether solution at −35° C. $^1$H NMR (C$_6$D$_6$, 500 MHz): δ 7.65 (m, 4, Ar), 7.46 (m, 1, Ar), 7.22 (m, 6, Ar), 7.04 (m, 6, Ar), 6.87 (td, 1, Ar), 6.65 (t, 2, Ar), 6.24 (t, 1, Ar), 5.99 (dd, 1, Ar), 4.11 (septet, 2, CHMe$_2$), 1.44 (d, 6, CHMe$_2$), 1.25 (d, 6, CHMe$_2$), 0.38 (d, 9, 2J$_{HP}$) 8, PMe$_3$). $^{31}$P{$^1$H}NMR (C$_6$D$_6$, 202.3 MHz): δ 33.00 (d, 2J$_{PP}$) 288, NP}, −22.32 (d, 2J$_{PP}$) 288, PMe$_3$}. $^{31}$P{$^1$H}NMR (THF, 121.42 MHz): δ 33.16 (d, 2J$_{PP}$) 286, NP}, −21.24 (d, 2J$_{PP}$) 293, PMe$_3$}. $^{13}$C{$^1$H}NMR (C$_6$D$_6$, 125.679 MHz): δ 168.56 (d, J$_{CP}$) 33.68), 151.90 (dd, 2J$_{CP}$) 39.1, $^2$J$_{CP}$) 33.7, NiC), 147.99, 145.89, 139.00 (CH), 134.7 (CH), 133.72 (CH), 133.18 (CH), 132.98 (d, J$_{CP}$) 50.90), 130.19 (CH), 128.67 (CH), 128.20 (CH), 126.73 (CH), 124.95 (CH), 121.97 (CH), 115.14 (d, J$_{CP}$) 44.62), 114.53 (d, J$_{CP}$) 12.69, CH), 112.54 (d, J$_{CP}$) 7.29, CH), 29.13 (CHMe$_2$), 25.04 (CHMe$_2$), 24.31 (CHMe$_2$), 13.45 (d, 1J$_{CP}$) 23.6, PMe$_3$).

Synthesis of [$^i$Pr-NP]Ni(η$_3$-CH$_2$Ph). Method 1: Solid [$i$-Pr-NP]NiCl$_2$ (500 mg, 0.47 mmol) was dissolved in THF (5 mL) and cooled to −35° C. To this was added dropwise a solution of PhCH$_2$MgCl (0.94 mL, 1.0MEt$_2$O solution, Aldrich, 0.94 mmol, 1 equiv per nickel). The reaction mixture was stirred at room temperature overnight and evaporated to dryness. The resulting residue was dissolved in CH$_2$Cl$_2$ (5 mL) and filtered through a pad of Celite. All volatiles were removed in vacuo to give a brownish red solid; yield 519 mg (94%). Method 2: Solid [$^i$Pr-NP]NiCl(PMe$_3$) (76.6 mg, 0.126 mmol) was dissolved in THF (2 mL) and cooled to −35° C. To this was added dropwise a solution of PhCH$_2$MgCl (0.13 mL, 1.0MEt$_2$O solution, Aldrich, 0.13 mmol). The reaction mixture was stirred at room temperature overnight and evaporated to dryness under reduced pressure. The resulting residue was dissolved in benzene (5 mL) and filtered through a pad of Celite. All volatiles were removed in vacuo to give a brownish red solid; yield 63.8 mg (86%). Method 3: A solid mixture of [$^i$Pr-NP]-Li(THF)$_2$ (200 mg, 0.341 mmol) and Ni(COD)$_2$ (93.72 mg, 0.341 mmol) was dissolved in THF (6 mL) at room temperature. To this was added a toluene solution of PhCH$_2$Cl (3.41 mL, 0.1 M, 0.341 mmol) at room temperature. After being stirred at room temperature for 3 h, the reaction mixture was evaporated to dryness under reduced pressure. The reddish brown solid residue was extracted with benzene (6 mL) and filtered through a pad of Celite. Solvent was removed in vacuo to afford the product as a brownish red solid; yield 178.5 mg (89%). Crystals suitable for X-ray diffraction analysis were grown by slow evaporation of a concentrated benzene solution at room temperature. $^1$H NMR (C$_6$D$_6$, 500 MHz): δ 7.67 (m, 4, Ar), 7.22 (m, 3, Ar), 7.06 (m, 7, Ar), 6.85 (t, 1, Ar), 6.66 (t, 1, Ar), 6.57 (t, 2, Ar), 6.24 (t, 1, Ar), 6.14 (d, 2, Ar), 6.04 (t, 1, Ar), 3.46 (septet, 2, CHMe$_2$), 1.56 (d, 2, 3J$_{HP}$) 4, NiCH$_2$Ph), 1.12 (d, 12, CHMe$_2$). $^1$H NMR (toluene-d8, 500 MHz): δ 7.64 (m, 4, Ar), 7.14 (m, 4, Ar), 7.07 (m, 4, Ar), 7.00 (m, 2, Ar), 6.80 (t, 1, Ar), 6.63 (m, 1, Ar), 6.55 (t, 2, Ar), 6.18 (t, 1, Ar), 6.11 (d, 2, Ar), 5.96 (t, 1, Ar), 3.41 (septet, 2, J) 7.5, CHMe$_2$), 1.52 (d, 2, 3J$_{HP}$) 3.5, NiCH$_2$), 1.12 (d, 6, J) 7.5, CHMe$_2$), 1.09 (d, 6, J) 7.5, CHMe$_2$). $^{31}$P-{$^1$H}NMR (C$_6$D$_6$, 202.5 MHz): δ 36.24. $^{31}$P{$^1$H}NMR (THF, 121.4 MHz): δ 36.27. $^{13}$C NMR (C$_6$D$_6$, 125.5 MHz): δ 168.11, 150.87, 145.36, 134.58 (CH), 134.35, 134.12, 133.30 (CH), 133.21 (CH), 130.62 (CH), 129.24 (J$_{CP}$) 9.91, CH), 126.82 (CH), 124.42 (CH), 123.97 (CH), 117.45, 114.82 (CH), 114.73 (CH), 112.42 (J$_{CP}$) 7.28, CH), 110.28 (J$_{CP}$) 5.52, CH), 28.71 (CHMe$_2$), 28.53 (2J$_{CP}$) 9.04, 1J$_{CH}$) 152, NiCH$_2$Ph), 24.26 (CHMe$_2$). Anal. Calcd for C$_{37}$H$_{38}$NNiP: C, 75.79; H, 6.53; N, 2.39. Found: C, 75.76; H, 6.75; N, 2.33.

Synthesis of [Me-NP]Ni(η$_3$-CH$_2$Ph). Diethyl ether (6 mL) was added to a solid mixture of [Me-NP]Li(THF)$_2$ (200 mg, 0.38 mmol) and Ni(COD)$_2$ (103.5 mg, 0.38 mmol). To this suspension was added PhCH$_2$Cl (3.8 mL, 0.1 M stock solution in diethyl ether, 0.38 mmol) at room temperature. The reaction mixture was stirred at room temperature for 3 h. All volatiles were removed in vacuo. The product was extracted from the resulting solid residue with benzene (3 mL_2). The deep brown solution was filtered through a pad of Celite, which was further washed with benzene (2 mL) until the washings were colorless. The combined filtrate was evaporated to dryness in vacuo to afford the product as a red solid; yield 188.2 mg (100%). Crystals suitable for X-ray diffraction analysis were grown by slow evaporation of a concentrated benzene solution at room temperature. $^1$H NMR (C$_6$D$_6$, 500 MHz): δ 7.76-7.80 (m, 4, Ar), 7.23 (d, 2, Ar), 7.12-7.20 (m, 7, Ar), 7.07 (t, 1, Ar), 6.92 (m, 1, Ar), 6.65 (m, 1, Ar), 6.56 (t, 2, Ar), 6.32 (t, 1, Ar), 6.10 (dd, 1, Ar), 6.06 (d, 2, Ar), 2.17 (s, 6, CH3), 1.55 (d, 2, 3J$_{HP}$) 4, NiCH$_2$Ph). $^{31}$P{C$_6$D$_6$} NMR (C$_6$D$_6$, 121.5 MHz): δ 34.84. $^{13}$C NMR (C$_6$D$_6$, 125.5 MHz): δ 166.67 (J$_{CP}$) 26.13), 151.91, 135.73, 134.63 (J$_{CP}$) 50.5), 134.06 (CH), 133.93 (CH), 133.49 (CH), 133.20 (J$_{CP}$) 11.75, CH), 130.57 (J$_{CP}$) 2.75, CH), 129.31 (J$_{CP}$) 10.75, CH), 128.68 (CH), 127.11 (J$_{CP}$) 2.63, CH), 123.42 (CH), 116.00, 114.69 (J$_{CP}$) 50.5), 112.50 (J$_{CP}$) 26.13, CH), 112.48 (J$_{CP}$) 8.13, CH), 110.60 (J$_{CP}$) 6.25, CH), 28.24 (2J$_{CP}$) 9.13, 1J$_{CH}$) 154, NiCH$_2$Ph), 18.92 (1J$_{CH}$) 122, CH$_3$). Anal. Calcd for C$_{33}$H$_{30}$NNiP: C, 74.75; H, 5.70; N, 2.64. Found: C, 73.73; H, 5.87; N, 2.63.

EXAMPLE 4

Synthesis of [MeNP]AlZ or [$^i$Pr-NP]AlZ

General Procedures. Unless otherwise specified, all experiments were performed under nitrogen using standard Schlenk or glovebox techniques. All solvents were reagent grade or better and purified by standard methods. The NMR spectra were recorded on Varian instruments. Chemical shifts (δ) are listed as parts per million downfield from tetramethylsilane, and coupling constants (J) and peak widths at half-height (Δv$_{1/2}$) are in hertz. $^1$H NMR spectra are referenced using the residual solvent peak at δ 7.16 for C$_6$D$_6$, δ 7.27 for CDCl$_3$, and δ 2.09 for toluene-d8 (the most upfield resonance). $^{13}$C NMR spectra are referenced using the residual solvent peak at δ 128.39 for C$_6$D$_6$ and δ 77.23 for CDCl$_3$. The assignment of the carbon atoms for all new compounds is based on DEPT $^{13}$C NMR spectroscopy. $^{19}$F, $^{31}$P, and $^{27}$Al NMR spectra are referenced externally using CFCl$_3$ in CHCl$_3$ at (0, 85% H$_3$PO$_4$ at δ 0, and AlCl$_3$ in D$_2$O at δ 0, respectively. Routine coupling constants are not listed. All NMR spectra were recorded at room temperature in specified solvents unless otherwise noted. The $^1$H-$^{31}$P correlation experiments were carried out on a Varian Inova 500 MHz instrument using HMBC sequence. The NOE data were obtained with a $^1$H NMR NOEDIF experimental apparatus. Elemental analysis was performed on a Heraeus CHN—O Rapid analyzer. For some aluminum complexes, we were not able to obtain satisfactory analysis due to extreme air and moisture sensitivity of these compounds.

Materials. Compounds N-(2-fluorophenyl)-2,6-diisopropylaniline, N-(2-diphenylphosphinophenyl)-2,6-diisopropylaniline (H[$^i$Pr-NP]), and [$^i$Pr-NP]Li(THF)$_2$ were prepared according to the procedures reported previously. All other chemicals were obtained from commercial vendors and used as received.

X-ray Crystallography. Data for compounds H[Me-NP] and [Me-NP]AlCl$_2$(THF) were collected on a Bruker SMART 1000 CCD diffractometer with graphite monochromated Mo Kα radiation (i) 0.7107 Å). Structures were solved by direct methods and refined by full-matrix least-squares procedures against F$^2$ using SHELXTL. All full-weight nonhydrogen atoms were refined anisotropically. Hydrogen atoms were placed in calculated positions. Data for compounds [Me-NP]AlEt$_2$ and [$^i$Pr-NP]AlMe$_2$ were collected on a Bruker-Nonius Kappa CCD diffractometer with graphite monochromated Mo Kα radiation (i) 0.7107 Å). Structures were solved by direct methods and refined by full-matrix least-squares procedures against F$^2$ using maXus. All full-weight non-hydrogen atoms were refined anisotropically. Hydrogen atoms were placed in calculated positions. The crystals of [Me-NP]AlEt$_2$ were of poor quality but sufficient to establish the identity of this molecule. The data set contains too many weak reflections, resulting in relatively high R-values.

Synthesis of N-(2-Fluorophenyl)-2,6-dimethylaniline. A 100-mL Schlenk flask was charged with 1-bromo-2-fluorobenzene (15.584 g, 89.05 mmol), 2,6-dimethylaniline (13.034 g, 107.56 mmol, 1.2 equiv), Pd(OAc)$_2$ (0.100 g, 0.445 mmol, 0.5% equiv), bis[2-(diphenylphosphino)phenyl]ether (DPEphos, 0.36 g, 0.668 mmol, 0.75% equiv), NaO$^t$Bu (12.0 g, 125 mmol, 1.4 equiv), and toluene (30 mL) under nitrogen. The reaction mixture was heated to reflux for 1 day. Toluene was removed in vacuo, and the reaction was quenched with deionized water (150 mL). The product was extracted with CH$_2$Cl$_2$ (200 mL), and the organic portion was separated from the aqueous layer, which was further extracted with CH$_2$Cl$_2$ (15 mL_2). The combined organic solution was dried over MgSO$_4$ and filtered. All volatiles were removed in vacuo to yield orange viscous oil, which was subjected to flash column chromatography on silica gel (9:1 hexanes/Et$_2$O). The first band (pale yellow) was collected. Solvents were removed in vacuo to give a yellowish orange solid; yield 12.23 g (64%). $^1$H NMR (CDCl$_3$, 200 MHz) δ 7.07-7.13 (m, 4, Ar), 6.87 (t, 1, Ar), 6.65 (m, 1, Ar), 6.22 (t, 1, Ar), 5.35 (br s, 1, NH), 2.22 (s, 6, CH$_3$). $^{19}$F NMR (CDCl$_3$, 470.5 MHz) δ-138.42. $^{13}$C NMR (CDCl$_3$, 125.5 MHz) δ 151.5 (J$_{CF}$) 237.4, CF), 137.2, 136.3, 134.7 (J$_{CF}$) 10.9, FCCN), 128.6 (CH), 126.3 (CH), 124.4 (J$_{CF}$) 2.8, CH), 117.4 (J$_{CF}$) 7.3, CH), 114.7 (J$_{CF}$) 18.1, CH), 113.1 (J$_{CF}$) 3.6, CH), 18.2 (CH$_3$). Anal. Calcd for C$_{14}$H$_{14}$FN: C, 78.11; H, 6.56; N, 6.51. Found: C, 77.88; H, 6.61; N, 6.48.

Synthesis of N-(2-Diphenylphosphinophenyl)-2,6-dimethylaniline, H[Me-NP]. A 100-mL Schlenk flask equipped with a condenser was flashed with nitrogen thoroughly. To this flask was added KPPh$_2$ (110 mL, 0.5 M in THF solution, Aldrich, 55.0 mmol). THF was removed in vacuo, and a solution of -(2-fluorophenyl)-2,6-dimethylaniline (10.6 g, 49.26 mmol) in DME (50 mL) was added with a syringe. The transparent, ruby reaction solution was heated to reflux for 2 days, during which time the reaction condition was monitored by $^{31}$P{$^1$H}NMR spectroscopy. All volatiles were removed from the resulting orange solution under reduced pressure, and degassed deionized water (140 mL) was added. The product was extracted with deoxygenated dichloromethane (100 mL). The dichloromethane solution was separated from the aqueous layer, from which the product was further extracted with dichloromethane (20 mL_2). The combined organic solution was dried over MgSO4 and filtered. All volatiles were removed in vacuo to yield a yellow solid. The yellow solid was purified by washing it with boiling MeOH (40 mL_3) until it became a white powder; yield 15.98 g (85%). $^1$H NMR (CDCl$_3$, 200 MHz) δ 7.41-7.60 (m, 10, PC$_6$H$_5$), 7.07-7.14 (m, 4, Ar), 6.89 (t, 1, Ar), 6.71 (t, 1, Ar), 6.20 (m, 1, Ar), 5.90 (d, 1, NH), 2.03 (s, 6, CH$_3$). $^1$H NMR (C$_6$D$_6$, 500 MHz) δ 7.47 (m, 4, Ar), 7.11 (td, 1, Ar), 7.06 (m, 6, Ar), 6.94 (m, 4, Ar), 6.61 (t, 1, Ar), 6.31 (m, 1, Ar), 6.04 (d, 1, J$_{HP}$) 7, NH}, 1.98 (s, 6, CH$_3$). $^{13}$P{$^1$H}NMR (C$_6$D$_6$, 202 MHz) δ−19.3. $^{31}$P{$^1$H}NMR (Et$_2$O, 121.5 MHz) δ−18.9. $^{31}$P{$^1$H}NMR (CDCl$_3$, 121.5 MHz) δ−19.1. $^{13}$C{$^1$H}NMR (CDCl$_3$, 75.3 MHz) δ 148.6 (J$_{CP}$) 17.0), 138.2, 135.8, 135.2, 135.1, 134.1, 133.8, 130.3, 128.8 (J$_{CP}$) 18.8), 128.5 (J$_{CP}$) 13.5), 125.6, 119.9 (J$_{CP}$) 9.1), 118.2, 111.8, 18.2 (CH$_3$). Anal. Calcd for C$_{26}$H$_{24}$NP: C, 81.87; H, 6.34; N, 3.67. Found: C, 81.45; H, 6.42; N, 3.61

General Procedures for the Synthesis of [Me-NP]AlR$_2$ and [$^i$Pr-NP]AlR$_2$ (R=Me, Et). A Teflon-sealed reaction vessel was charged with a toluene solution containing an appropriate ligand precursor and 1 equiv of AlMe$_3$ (Aldrich, 2.0 M in toluene) or AlEt$_3$ (TCI, 15% in toluene). The colorless solution was heated to 110° C. for 2 days. Evaporation of the resulting yellow solution to dryness under reduced pressure afforded the product as pale-yellow microcrystals, which were recrystallized from 1:1 THF/Et$_2$O to give pale-yellow crystals.

Synthesis of [Me-NP]AlMe$_2$. Yield 93%. $^1$H NMR (C$_6$D$_6$, 500 MHz) δ 7.40 (m, 4, Ar), 6.97-7.20 (m, 1, Ar), 6.42 (t, 1, Ar), 6.23 (t, 1, Ar), 2.22 (s, 6, C$_6$H$_3$Me2), −0.24 (d, 6, AlCH$_3$, 3 J$_{HP}$=4). $^{13}$C{$^1$H}NMR (C$_6$D$_6$, 125.70 MHz) δ 160.8 (d, J$_{CP}$=20.1, C), 144.5 (d, J$_{CP}$=4.5, C), 137.5 (C), 135.2 (CH), 134.9 (CH), 134.0 (d, J$_{CP}$=12.8, CH), 131.1 (d, J$_{CP}$=1.8, CH), 129.7 (CH), 129.6 (d, J$_{CP}$=9.9, CH), 125.7 (CH), 116.1 (d, J$_{CP}$=5.5, CH), 114.7 (d, J$_{CP}$=6.4, CH), 110.9 (C), 110.6 (C), 19.3 (Ar CH$_3$), −8.7 (d, 2 J$_{CP}$=22, AlCH$_3$). $^{31}$P{$^1$H}NMR (C$_6$D$_6$, 202.31 MHz) δ−24.1 (Δν$_{1/2}$) 6 Hz). $^{27}$Al NMR (C$_6$D$_6$, 130.22 MHz) δ 158 (Δν$_{1/2}$) 10 289 Hz). LRMS (EI) Calcd for C$_{28}$H$_{29}$AlNP m/z 437, found m/z 437. Anal. Calcd for C$_{28}$H$_{29}$AlNP: C, 76.87; H, 6.68; N, 3.20. Found: C, 73.95; H, 6.53; N, 3.22.

Synthesis of [$^i$Pr-NP]AlMe$_2$. Yield 96%. $^1$H NMR (C$_6$D$_6$, 500 MHz) δ 7.38 (m, 4, Ar), 7.22 (m, 3, Ar), 7.01 (m, 7, Ar), 6.90 (t, 1, Ar), 6.40 (t, 1, Ar), 6.23 (t, 1, Ar), 3.35 (septet, 2, CHMe$_2$), 1.12 (d, 6, CHMe$_2$), 1.04 (d, 6, CHMe$_2$), −0.23 (d, 6, Al CH$_3$, 3 J$_{HP}$=4). $^{13}$C{$^1$H}NMR (C$_6$D$_6$, 125.70 MHz) δ 162.2 (d, J$_{CP}$=19.1, C), 148.0 (C), 141.9 (d, JCP 4.5, C), 134.8 (CH), 134.7 (CH), 134.1 (CH), 131.1 (d, J$_{CP}$=1.8, CH), 129.5 (d, J$_{CP}$=10.0, CH), 12.7 (CH), 125.0 (CH), 117.1 (d, J$_{CP}$=6.4, CH), 116.6 (d, J$_{CP}$=6.4, CH), 112.0 (C), 111.6 (C), 28.4 (CHMe$_2$), 25.6 (CHMe$_2$), 25.2 (CHMe$_2$), −9.1 (d, 2 J$_{CP}$=20, AlCH$_3$). $^{31}$P{$^1$H}NMR (C$_6$D$_6$, 202.31 MHz) δ−21.6 (Δν$_{1/2}$) 7 Hz). 27Al NMR (C$_6$D$_6$, 130.22 MHz) δ 151 (Δν$_{1/2}$) 10 023 Hz). Anal. Calcd for C$_{32}$H$_{37}$AlNP: C, 77.87; H, 7.56; N, 2.84. Found: C, 77.19; H, 7.53; N, 2.88.

Synthesis of [Me-NP]AlEt$_2$. Yield 98%. $^1$H NMR (C$_6$D$_6$, 500 MHz) δ 7.46 (m, 4, Ar), 7.10 (m, 2, Ar), 7.06 (m, 1, Ar), 6.97-7.04 (m, 7, Ar), 6.94 (m, 1, Ar), 6.42 (t, 1, Ar), 6.23 (t, 1, Ar), 2.23 (s, 6, C$_6$H$_3$Me$_2$), 1.20 (t, 6, AlCH$_2$CH$_3$), 0.43 (m, 4, AlCH$_2$). $^1$H NMR (C$_7$D$_8$, 500 MHz) δ 7.35 (m, 4, Ar), 6.91 (m, 10, Ar), 6.80 (t, 1, Ar), 6.30 (t, 1, Ar), 6.07 (t, 1, Ar), 2.09 (s, 6, C$_6$H$_3$Me$_2$), 1.05 (t, 6, AlCH$_2$CH$_3$), 0.28 (m, 4, AlCH$_2$). $^{13}$C{$^1$H}NMR (C$_6$D$_6$, 125.70 MHz) δ 161.1 (CH, J$_{CP}$=20.8, C), 144.8 (d, J$_{CP}$=4.5, C), 137.3 (C), 135.1 (CH), 134.8 (CH), 133.9 (d, J$_{CP}$=12.7, CH), 131.1 (d, J$_{CP}$=2.8, CH), 129.6 (CH), 129.5 (CH), 126.7 (CH), 116.2 (d, J$_{CP}$=6.4, CH), 114.8 (d, J$_{CP}$=6.4, CH), 110.7 (C), 110.4 (C), 19.2 (ArCH$_3$), 9.8 (d, 3 J$_{CP}$=1.9, 1CH$_2$CH$_3$), 0.9 (d, 2 J$_{CP}$=18, AlCH2). $^{31}$P{$^1$H}NMR (C$_6$D$_6$, 202.31 MHz) δ−24.0 (Δν$_{1/2}$) 4 Hz}. 27Al NMR (C$_6$D$_6$, 130.22 MHz) δ 158 (Δν$_{1/2}$) 12 763 Hz}.

Synthesis of [$^i$Pr-NP]AlEt$_2$. Yield 92%. $^1$H NMR (C$_6$D$_6$, 500 MHz) δ 7.39 (m, 4, Ar), 7.16 (m, 3, Ar), 6.95-7.00 (m, 7, Ar), 6.84 (m, 1, Ar), 6.36 (t, 1, Ar), 6.18 (t, 1, Ar), 3.28 (septet, 2, CHMe$_2$), 1.18 (t, 6, AlCH$_2$CH$_3$), 1.10 (d, 6, CHMe$_2$), 0.98 (d, 6, CHMe$_2$), 0.48 (m, 2, AlCHAHB, 2J$_{HH}$=15), 0.37 (m, 2, AlCHAHB, 3 J$_{HP}$=7, 2J$_{HH}$=15). $^1$H NMR (C7D8, 500 MHz) δ 7.44 (m, 4, Ar), 7.21 (m, 3, Ar), 7.02 (m, 7, Ar), 6.89 (t, 1, Ar), 6.41 (t, 1, Ar), 6.24 (t, 1, Ar), 3.32 (septet, 2, CH Me$_2$), 1.22 (t, 6, AlCH$_2$CH$_3$), 1.15 (d, 6, CHMe$_2$), 1.03 (d, 6, CHMe$_2$), 0.53 (m, 2, AlCHAHB), 0.42 (m, 2, AlCHAHB). $^{13}$C{$^1$H}NMR (C$_6$D$_6$, 125.70 MHz) δ 162.5 (d, J$_{CP}$=20.0, C), 147.7 (C), 142.4 (d, J$_{CP}$) 4.5, C), 134.7 (CH), 134.7 (CH), 134.0 (CH), 131.1 (d, J$_{CP}$=1.8, CH), 129.5 (d, J$_{CP}$=10.0, CH), 129.5 (CH), 126.6 (CH), 125.0 (CH), 117.3 (d, J$_{CP}$=5.4, CH), 116.6 (d, J$_{CP}$=5.4, CH), 111.8 (C), 111.5 (C), 28.4 (CH Me$_2$), 25.8 (CHMe$_2$), 24.9 (CHMe$_2$), 9.8 (d, 3 J$_{CP}$) 1.8, AlCH$_2$CH$_3$}, 0.2 (d, 2 J$_{CP}$=20, AlCH2). $^{31}$P{$^1$H}NMR (C$_6$D$_6$, 202.31 MHz) δ−21.4 (Δν$_{1/2}$) 4 Hz). 27Al NMR (C$_6$D$_6$, 130.22 MHz) δ 151.8 (Δν$_{1/2}$) 12 565 Hz). The coupling constants 2J$_{HH}$ and 3 J$_{HP}$ were determined by $^1$H NMR spectroscopy with selective decoupling of α-hydrogen atoms. LRMS (EI) Calcd for C$_{34}$H$_{41}$AlNP m/z 521, found m/z 521.

Synthesis of [Me-NP]AlCl$_2$. To a solution of H[Me-NP] (2.0 g, 5.24 mmol) in THF (15 mL) at −35° C. was added n-BuLi (3.3 mL, 5.24 mmol, 1 equiv). The reaction mixture was naturally warmed to room temperature and stirred for 3 h. All volatiles were removed in vacuo. The red viscous residue was triturated with pentane (15 mL) to yield a yellow solid. The yellow solid was isolated from the orange solution, washed with pentane (5 mL_3), and dried in vacuo to give [Me-NP]Li(THF)$_2$ as indicated by 1H$^1$H NMR spectroscopy; yield 2.67 g (99%). $^1$H NMR (C$_6$D$_6$, 500 MHz) δ 7.58 (m, 4, Ar), 7.23 (d, 2, Ar), 7.07-7.16 (m, 8, Ar), 6.97 (m, 1, Ar), 6.38 (m, 1, Ar), 6.33 (m, 1, Ar), 3.23 (m, 8, OCH$_2$—CH$_2$), 2.26 (s, 6, CH$_3$), 1.19 (m, 8, OCH$_2$CH$_2$). Solid AlCl$_3$ (2.600 g, 1.950 mmol) was added in portions to a solution of [Me-NP]Li(THF)$_2$ (1.00 g, 1.881 mmol) in toluene (15 mL) at −35° C. The reaction mixture was stirred at room temperature for 4 days and filtered through a pad of Celite. Solvent was stripped from the filtrate to afford an off-white solid; yield 905 mg (100%). $^1$H NMR (C$_6$D$_6$, 500 MHz) δ 7.53 (m, 4,Ar), 6.94-7.04 (m, 10, Ar), 6.89 (t, 1, Ar), 6.44 (t, 1, Ar), 6.22 (t, 1, Ar), 2.32 (s, 6, CH$_3$). $^{13}$C{$^1$H} NMR (C$_6$D$_6$, 125.5 MHz) δ 159.2 (d, J$_{CP}$=16.4, C), 143.0 (d, J$_{CP}$=5.4, C), 138.0 (C), 135.2 (CH), 134.4 (CH), 134.4 (CH), 131.7 (d, J$_{CP}$=2.8, CH), 129.8 (CH), 129.7 (d, J$_{CP}$=3.6, CH), 126.6 (CH), 126.2 (C), 118.2 (d, J$_{CP}$=6.3, CH), 115.2 (d, J$_{CP}$=5.4, CH), 110.4 (d, J$_{CP}$=46.3, C), 19.4 (Me). $^{31}$P{$^1$H} NMR (C$_6$D$_6$, 121.5 MHz) δ−36.1 (Δν$_{1/2}$) 137 Hz}. $^{27}$Al NMR (C$_6$D$_6$, 130.22 MHz) δ 94 (Δν$_{1/2}$) 293 Hz}. Recrystallization of [Me-NP]AlCl$_2$ from THF at −35° C. produced the solvated compound [Me-NP]-AlCl$_2$(THF) as colorless crystals suitable for X-ray crystallography. The recrystallization yield is typically 70%. $^1$H NMR (C$_6$D$_6$, 500 MHz) δ 7.76 (m, 4, Ar), 7.14 (m, 1, Ar), 7.04 (m, 6, Ar), 6.97 (m, 2, Ar), 6.92 (m, 2, Ar), 6.50 (t, 1, Ar), 6.18 (t, 1, Ar), 3.58 (m, 4, OCH$_2$CH$_2$), 2.30 (s, 6, CH$_3$), 1.12 (m, 4, OCH$_2$CH$_2$). $^{13}$C{$^1$H}NMR (C$_6$D$_6$, 125.5 MHz) δ 159.2 (d, J$_{CP}$=20.3, C), 146.2 (d, J$_{CP}$=6.4, C), 138.5 (C), 135.9 (CH), 134.6 (d, J$_{CP}$=11.3, CH), 134.1 (CH), 130.8 (C), 130.5 (CH), 129.5 (CH), 129.1 (d, J$_{CP}$=9.5, CH), 126.0 (CH), 118.0 (d, J$_{CP}$=5.0, CH), 115.1 (d, J$_{CP}$=5.9, CH), 113.3 (d, J$_{CP}$=35.3, C), 71.1 (OCH$_2$CH$_2$), 25.3 (OCH$_2$CH$_2$), 19.3 (Me). $^{31}$P{$^1$H} NMR (C$_6$D$_6$, 121.5 MHz) δ−34.8 (Δν$_{1/2}$) 54 Hz). 27Al NMR (C$_6$D$_6$, 130.22 MHz) δ 74 (Δν$_{1/2}$) 351 Hz}.

Synthesis of [$^i$Pr-NP]AlCl$_2$. Solid AlCl$_3$ (250 mg, 1.8749 mmol) was added in portions to a solution of [$i$Pr-NP]Li (THF)$_2$ (1.0658 g, 1.8157 mmol) in toluene (15 mL) at −35° C. The reaction mixture was stirred at room temperature for 4 days and filtered through a pad of Celite. Concentration of the filtrate under reduced pressure afforded [$^i$Pr-NP]AlCl$_2$ as colorless crystals which were isolated by filtration and dried in vacuo; yield 951 mg (98.1%). $^1$H NMR (C$_6$D$_6$, 500 MHz) δ 7.38 (m, 4, Ar), 7.13 (m, 3, Ar), 6.95 (m, 2, Ar), 6.89 (m, 4, Ar), 6.79 (m, 2, Ar), 6.34 (t, 1, Ar), 6.22 (t, 1, Ar), 3.38 (septet, 2, CH Me$_2$), 1.18 (d, 6, CHMe$_2$), 0.95 (d, 6, CHMe$_2$). $^{13}$C{$^1$H}NMR (C$_6$D$_6$, 125.70 MHz) δ 160.5 (d, J$_{CP}$=14.6, C), 148.2 (C), 139.0 (d, J$_{CP}$=3.6, C), 135.1 (CH), 134.5 (CH), 134.5 (CH), 132.2 (d, J$_{CP}$=2.8, CH), 129.8 (d, J$_{CP}$=10.8, CH), 127.7 (CH), 125.3 (CH), 124.4 (d, J$_{CP}$=51.8, C), 118.7 (d, J$_{CP}$=6.3, CH), 117.6 (d, J$_{CP}$=5.4, CH), 109.9 (d, J$_{CP}$=51.0, C), 28.7 (CHMe$_2$), 25.5 (CHMe$_2$), 25.3 (CHMe$_2$). $^{31}$P{$^1$H}NMR (C$_6$D$_6$, 202.31 MHz) δ−34.4 (Δν$_{1/2}$) 180 Hz}. 27Al NMR (C$_6$D$_6$, 130.22 MHz) δ 99 (Δν$_{1/2}$) 295 Hz}. Recrystallization of [$^i$Pr-NP]AlCl$_2$ from THF at −35° C. afforded [$^i$Pr-NP]AlCl$_2$(THF) as colorless crystals. $^1$H NMR (C$_6$D$_6$, 500 MHz) δ 7.55 (m, 4, Ar), 7.16 (m, 5, Ar), 7.02 (m, 5, Ar), 6.93 (t, 1, Ar), 6.42 (t, 1, Ar), 6.19 (t, 1, Ar), 3.88 (m, 4, OCH$_2$CH$_2$) 3.44 (septet, 2, CHMe$_2$), 1.19 (m, 4, OCH$_2$CH$_2$), 1.14 (d, 6, CHMe$_2$), 0.97 (d, 6, CHMe$_2$). $^{13}$C{$^1$H}NMR (C$_6$D$_6$, 125.70 MHz) δ 159.8 (d, J$_{CP}$=17.2, C), 147.8 (C), 140.2 (d, J$_{CP}$=4.5, C), 134.2 (CH), 134.0 (CH), 133.9 (CH), 130.8 (d, J$_{CP}$=2.6, CH), 128.8 (d, J$_{CP}$=10.0, CH), 126.8 (CH), 124.6 (CH), 117.8 (d, J$_{CP}$) 6.4, CH}, 117.0 (d, J$_{CP}$=5.5, CH), 110.9 (C), 110.5 (C), 71.1 (OCH$_2$CH$_2$), 27.9 (CHMe$_2$), 25.1 (CHMe$_2$), 24.8 (OCH$_2$CH$_2$), 24.2 (CHMe$_2$). $^{31}$P{$^1$H}NMR (C$_6$D$_6$, 202.31 MHz) d-33.7 (Δν$_{1/2}$) 85 Hz). $^{27}$Al NMR (C$_6$D$_6$, 130.22 MHz) δ 69 (Δν$_{1/2}$) 387 Hz). Anal. Calcd for C$_{30}$H$_{31}$AlCl$_2$NP: C, 67.42; H, 5.85; N, 2.62. Found: C, 66.99; H, 7.07; N, 2.47.

Synthesis of [Me-NP]Al(CH$_2$SiMe$_3$)$_2$. A pentane solution of LiCH$_2$SiMe$_3$ (1.1 mL, 1 M in pentane, Aldrich, 1.10 mmol, 2 equiv) was added dropwise to a solution of [Me-NP]AlCl$_2$ (300 mg, 0.55 mmol) in toluene (10 mL) at −35° C. The reaction mixture was stirred at room temperature for 2 days. The insoluble materials thus produced were removed by filtration with a short column of Celite. Solvent was stripped and the product was obtained as a pale yellow solid; yield 286 mg (90%). Recrystallization from diethyl ether afforded colorless crystals. $^1$H NMR (C$_6$D$_6$, 500 MHz), 7.46 (m, 4, Ar), 7.09 (m, 2, Ar), 7.02 (m, 8, Ar), 6.94 (m, 1, Ar), 6.43 (t, 1, Ar), 6.18 (t, 1, Ar), 2.21 (s, 6, C$_6$H$_3$Me$_2$), 0.028 (s, 18, SiMe3),−0.30 (d, 2, AlCHAHB, 2J$_{HH}$=13), −0.39 (dd, 2, AlCHAHB, 3 J$_{HP}$=7, 2 J$_{HH}$=13). $^{13}$C{$^1$H}NMR (C$_6$D$_6$, 125.70 MHz) δ 161.5 (d, J$_{CP}$=20.0, C), 145.0 (d, J$_{CP}$=5.5, C), 137.8 (C), 135.5 (CH), 134.9 (CH), 133.9 (d, J$_{CP}$=11.8, CH), 131.2 (d, J$_{CP}$=1.9, CH), 129.9 (CH), 129.6 (d, J$_{CP}$=10.0, CH), 126.0 (CH), 116.3 (d, J$_{CP}$=5.4, CH), 115.0 (d, J$_{CP}$=6.4, CH), 111.1 (C), 110.7 (C), 19.7 (ArCH$_3$), 3.4

(SiMe), -2.2 (d, 2 $J_{CP}$=16, AlCH$_2$). $^{31}$P{$^1$H}NMR (C$_6$D$_6$, 202.31 MHz) δ-24.2 (Δv$_{1/2}$) 5 Hz). $^{27}$Al NMR (C$_6$D$_6$, 130.22 MHz) δ 159 (Δv$_{1/2}$) 13 712 Hz). Anal. Calcd for C$_{34}$H$_{45}$ AlNPSi$_2$: C, 70.18; H, 7.80; N, 2.41. Found: C, 67.64; H, 6.99; N, 2.59.

EXAMPLE 5

Synthesis of [PNP]PdZ

General Procedures. Unless otherwise specified, all experiments were performed under nitrogen using standard Schlenk or glovebox techniques. All solvents were reagent grade or better and were purified by standard methods. The compound [PNP]Li(THF)$_2$ was prepared as above. All other chemicals were used as received from commercial vendors. The NMR spectra were recorded on Varian instruments. Chemical shifts (δ) are listed as parts per million downfield from tetramethylsilane, and coupling constants (J) are in hertz. $^1$H NMR spectra are referenced using the residual solvent peak at δ 7.16 for C$_6$D$_6$ and δ 7.27 for CDCl$_3$. 13C NMR spectra are referenced using the residual solvent peak at δ 128.39 for C$_6$D$_6$ and δ 7.23 for CDCl$_3$. The assignment of the carbon atoms for all compounds is based on DEPT $^{13}$C NMR spectroscopy. $^{31}$P NMR spectra are referenced externally using 85% H$_3$PO$_4$ at δ 0. Routine coupling constants are not listed. All NMR spectra were recorded at room temperature in specified solvents. Mass spectra were recorded on a Finnigan MAT 95XL mass spectrometer. Elemental analysis was performed on a Heraeus CHN—O Rapid analyzer. The Heck coupling reactions were analyzed by GC on a Varian Chrompack CP-3800 instrument equipped with a CP-Sil 5 CB Chrompack capillary column and the yields calculated versus aryl halides or dodecane as an internal standard. The identity of the products was confirmed by comparison with authentic samples.

X-ray Crystallography. Data for [PNP]PdCl (3a) were collected on a Bruker-Nonius Kappa CCD diffractometer with graphite-monochromated Mo Kα radiation (i) 0.7107 Å). Structures were solved by direct methods and refined by fullmatrix least-squares procedures against F2 using maXus. All full-weight non-hydrogen atoms were refined anisotropically. Hydrogen atoms were placed in calculated positions.

Synthesis of [PNP]PdCl. Solid PdCl$_2$(PhCN)$_2$ (100 mg, 0.261 mmol) was dissolved in THF (4 mL) and cooled to -35° C. To this was added dropwise a cold THF solution (4 mL) of [PNP]Li(THF)$_2$ (180 mg, 0.267 mmol) at -35° C. The reaction mixture was stirred at room temperature for 1 h and evaporated to dryness under reduced pressure. The residue was triturated with pentane (9 mL), extracted with CH$_2$Cl$_2$ (10 mL), and filtered through a pad of Celite. Solvent was removed in vacuo. The residue was washed with pentane (15 mL) and dried in vacuo to yield the product as a brick red solid; yield 149 mg (84%). Single crystals suitable for X-ray crystallography were grown from a concentrated benzene solution at room temperature. $^1$H NMR (C$_6$D$_6$, 500 MHz): δ 7.86 (m, 8, Ar), 7.78 (d, 2, Ar), 7.06 (m, 2, Ar), 6.93-6.99 (m, 10, Ar), 6.88 (t, 2, Ar), 6.63 (t, 2, Ar), 6.40 (t, 2, Ar). $^{31}$P{$^1$H}NMR (C$_6$D$_6$, 202.31 MHz): δ 29.79. $^{31}$P{$^1$H} NMR (THF, 80.95 MHz): δ 29.36. $^{13}$C{$^1$H} NMR (C$_6$D$_6$, 125.70 MHz): δ 163.18 (t, $J_{CP}$ 12.70, C), 136.15 (s, CH), 134.51 (t, $J_{CP}$) 6.79, CH), 132.52 (s, CH), 132.33 (t, $J_{CP}$) 5.40, C), 131.15 (t, $J_{CP}$) 11.82, CH), 129.33 (t, $J_{CP}$) 5.47, CH), 122.23 (t, $J_{CP}$) 23.19, C), 119.03 (br s, CH), 117.65 (t, $J_{CP}$) 6.85, CH). Anal. Calcd for C$_{36}$H$_{28}$ClNPdP$_2$: C, 63.73; H, 4.16; N, 2.06. Found: C, 63.14; H, 4.36; N, 2.10.

Synthesis of [PNP]Pd(OAc) (3b). Solid Pd(OAc)$_2$ (50 mg, 0.223 mmol) was dissolved in THF (4 mL) and cooled to -35° C. To this was added dropwise a cold THF solution (4 mL) of [PNP]Li(THF)$_2$ (153 mg, 0.223 mmol) at -35° C. The reaction mixture was stirred at room temperature for 1 h and evaporated to dryness under reduced pressure. The residue was triturated with pentane (9 mL), extracted with CH$_2$Cl$_2$ (10 mL), and filtered through a pad of Celite. Solvent was removed in vacuo. The residue was washed with pentane (15 mL) and dried in vacuo to yield the product as a brick red solid; yield 114 mg (73%). $^1$H NMR (C$_6$D$_6$, 500 MHz): δ 7.97 (m, 8, Ar), 7.66 (d, 2, Ar), 6.99-7.08 (m, 14, Ar), 6.83 (t, 2, Ar), 6.38 (t, 2, Ar), 1.93 (s, 3, CH$_3$). $^{31}$P{$^1$H}NMR (C$_6$D$_6$, 202.31 MHz): δ 29.12. $^{31}$P{$^1$H}NMR (THF, 80.95 MHz): δ 28.63. $^{13}$C{$^1$H}NMR (C$_6$D$_6$, 125.70 MHz): δ 175.43 (s, CdO), 162.89 (t, $J_{CP}$) 12.26, C), 135.26 (s, CH), 134.58 (t, $J_{CP}$) 7.29, CH), 132.38 (s, CH), 131.60 (t, $J_{CP}$) 24.51, C), 131.09 (s, CH), 129.26 (t, $J_{CP}$) 5.41, CH), 123.66 (t, $J_{CP}$) 23.13, C), 118.80 (br s, CH), 117.74 (t, $J_{CP}$) 5.91, CH), 23.24 (s, CH$_3$). Anal. Calcd for C$_{38}$H$_{31}$NO$_2$PdP$_2$: C, 65.01; H, 4.45; N, 2.00. Found: C, 63.77; H, 4.77; N, 1.95.

EXAMPLE 6

Carbon-Carbon Bond Formation Catalyzed by the Complex

General Procedures of Heck Reactions of aryl halides with styrene. A 100-mL Schlenk flask was sequentially charged with [PNP]PdCl (1.0 mg, 0.00147 mmol, 0.2% with respect to the halide), 1 equiv of aryl halide, MeNCy$_2$ (160.0 mg, 0.8190 mmol, 1.1 equiv), styrene (85.0 mg, 0.8161 mmol, 1.1 equiv), NMP (2 mL) and a magnetic stir bar. The flask was capped with a stopper and the reaction mixture was stirred in a 160° C. oil bath for 12 h. A reaction aliquot was taken and analyzed with GC, which showed quantitative formation of the olefinated product. After the reaction was cooled to room temperature, hydrochloric acid (1 M, 6 mL) was added to the reaction mixture the product was extracted with diethyl ether (15 mL×3). After being separated from the aqueous layer, the diethyl ether solution was further washed with deionized water (15 mL×3), dried over MgSO$_4$, and evaporated to dryness under reduced pressure. The residue was then washed with hexane (5 mL×3) and dried in vacuo to afford the product. The $^1$H and $^{13}$C NMR spectroscopic data of the coupled product are identical to those reported previously (Djakovitch, L.; Koehler, K. J. Am. Chem. Soc. 2001, 123, 5990-5999.).

Representative Example: Synthesis of 4-Acetylstilbene. A 100-mL Schlenk flask was sequentially charged with [PNP]PdCl (1.0 mg, 0.00147 mmol, 0.2% with respect to the bromide), 4-bromoacetophenone (147.0 mg, 0.7385 mmol, 1 equiv), MeNCy$_2$ (160.0 mg, 0.8190 mmol, 1.1 equiv), styrene (85.0 mg, 0.8161 mmol, 1.1 equiv), NMP (2 mL) and a magnetic stir bar. The flask was capped with a stopper and the reaction mixture was stirred in a 160° C. oil bath for 12 h. A reaction aliquot was taken and analyzed with GC, which showed quantitative formation of the olefinated product. After the reaction was cooled to room temperature, hydrochloric acid (1 M, 6 mL) was added to the reaction mixture and the product was extracted with diethyl ether (15 mL×3). After being separated from the aqueous layer, the diethyl ether solution was further washed with deionized water (15 mL×3), dried over MgSO$_4$, and evaporated to dryness under reduced pressure. The residue was then washed with hexane (5 mL×3) and dried in vacuo to afford the product as a colorless solid; yield 137.4 mg (83%). $^1$H NMR (CDCl$_3$, 500 MHz) δ 7.93 (d, 2, o-C$_6$H$_4$COMe, J$_{HH}$=8), 7.54 (d, 2, m-C$_6$H$_4$COMe, J$_{HH}$=8), 7.52 (d, 2, o-C$_6$H$_5$, J$_{HH}$=8), 7.37 (t, 2, m-C$_6$H$_5$, J$_{HH}$=7.5), 7.30 (t, 1, p-C$_6$H$_5$, J$_{HH}$=7), 7.19 (d, 1, vinyl-C$_6$H$_5$, J$_{HH}$=16.5), 7.09 (d, 2, vinyl-C$_6$H$_5$, J$_{HH}$=16.5), 2.57 (s, 3, COMe). $^{13}$C{$^1$H} NMR (CDCl$_3$, 125.70 MHz) δ 197.18 (s, COMe, C), 141.70 (s, p-C$_6$H$_4$COMe, C), 136.43 (s, C$_6$H$_4$COMe, COMe), 135.66 (s, C$_6$H$_5$, C), 131.17 (s, m-C$_6$H$_5$, CH), 128.63 (s, m-C$_6$H$_4$COMe, CH), 128.58 (s, o-C$_6$H$_4$COMe, CH), 128.10 (s, p-C$_6$H$_5$, CH), 127.16 (s, o-C$_6$H$_5$, CH), 126.63 (s, C=C, CH), 126.27 (s, C=C, CH), 26.33 (s, COMe, CH$_3$).

Synthesis of Stilbene. $^1$H NMR (CDCl$_3$, 500 MHz) δ 7.62 (d, 4, o-C$_6$H$_5$, J$_{HH}$=7.5), 7.46 (t, 4, m-C$_6$H$_5$, J$_{HH}$=7.5), 7.36 (t, 2, p-C$_6$H$_5$, J$_{HH}$=7.5), 7.22 (s, 2, vinyl-C$_6$H$_5$). $^{13}$C{$^1$H} NMR (CDCl$_3$, 125.70 MHz) δ 137.26 (s, C$_6$H$_5$, C), 128.64 (s, C=C, CH), 128.63 (s, m-C$_6$H$_5$, CH), 127.56 (s, p-C$_6$H$_5$, CH), 126.47 (s, o-C$_6$H$_5$, CH).

Synthesis of 4-Nitrostilbene. $^1$H NMR (CDCl$_3$, 500 MHz) δ 8.21 (d, 2, o-C$_6$H$_4$NO$_2$, J$_{HH}$=8.5), 7.62 (d, 2, m-C$_6$H$_4$NO$_2$, J$_{HH}$=8.5), 7.56 (d, 4, o-C$_6$H$_5$, J$_{HH}$=7.5), 7.41 (t, 2, m-C$_6$H$_5$, J$_{HH}$=7.5), 7.35 (t, 1, p-C$_6$H$_5$, J$_{HH}$=7), 7.27 (d, 1, vinyl-C$_6$H$_5$, J$_{HH}$=16), 7.14 (d, 2, vinyl-C$_6$H$_5$, J$_{HH}$=16.5). $^{13}$C{$^1$H} NMR (CDCl$_3$, 125.70 MHz) δ 146.65 (s, C$_6$H$_4$NO$_2$, C—N), 143.76 (s, p-C$_6$H$_4$NO$_2$, C), 136.09 (s, C$_6$H$_5$, C), 133.21 (s, m-C$_6$H$_5$, CH), 128.82 (s, o-C$_6$H$_4$NO$_2$, CH), 128.77 (s, p-C$_6$H$_5$, CH), 126.95 (s, C=C, CH), 126.77 (s, C=C, CH), 126.18 (s, o-C$_6$H$_5$, CH), 124.05 (s, m-C$_6$H$_4$NO$_2$, CH).

Synthesis of 4-Stilbenecarboxaldehyde. $^1$H NMR (CDCl$_3$, 500 MHz) δ 9.98 (s, 1, COH), 7.86 (d, 2, o-C$_6$H$_4$COH, J$_{HH}$=8.5), 7.63 (d, 2, m-C$_6$H$_4$COH, J$_{HH}$=8.5), 7.54 (d, 2, o-C$_6$H$_5$, J$_{HH}$=7.5), 7.39 (t, 2, m-C$_6$H$_5$, J$_{HH}$=7.5), 7.32 (t, 1, p-C$_6$H$_5$, J$_{HH}$=7), 7.24 (d, 1, vinyl-C$_6$H$_5$, J$_{HH}$=16.5), 7.12 (d, 2, vinyl-C$_6$H$_5$, J$_{HH}$=16.5). $^{13}$C{$^1$H} NMR (CDCl$_3$, 125.70 MHz) δ 191.47 (s, COH, C), 143.22 (s, p-C$_6$H$_4$COH, C), 136.37 (s, C$_6$H$_4$COH, COH), 135.14 (s, C$_6$H$_5$, C), 132.01 (s, m-C$_6$H$_5$, CH), 130.07 (s, m-C$_6$H$_4$COH, CH), 128.69 (s, o-C$_6$H$_4$COH, CH), 128.37 (s, p-C$_6$H$_5$, CH), 127.14 (s, o-C$_6$H$_5$, CH), 126.78 (s, C=C, CH), 126.75 (s, C=C, CH).

General Procedures for the Heck Reactions. A Schlenk flask was charged with 3a or 3b (1.0 mg for each single experiment) along with an appropriate amount of aryl halide (1.0 equiv), styrene (1.1 equiv), MeNCy2 (1.1 equiv), and NMP (2 mL) and a magnetic stir bar. The flask was capped with a stopper and heated in an oil bath at 160° C. with stirring for a specified period of time. After the reaction mixture was cooled to room temperature, hydrochloric acid (1M, 6 mL) was added and the product was extracted with diethyl ether (15 mL_3). The aqueous solution was separated from the organic layer. The diethyl ether solution was washed with deionized water (15 mL_3), dried over MgSO$_4$, and evaporated to dryness under reduced pressure to afford the desired product, which was then washed with hexane (5 mL_3) or subject to flash column chromatography on silica gel. For experiments with low catalyst loading (entries 2-5), stock solutions of appropriate concentrations were prepared by dissolving 1.0 mg of [PNP]PdCl in appropriate amounts of NMP and used for each independent run.

trans-Stilbene (Y=H). $^1$H NMR (CDCl$_3$, 500 MHz): δ 7.62 (d, 4, J$_{HH}$) 7.5, o-C$_6$H$_5$), 7.46 (t, 4, J$_{HH}$) 7.5, m-C$_6$H$_5$), 7.36 (t, 2, J$_{HH}$) 7.5, p-C$_6$H$_5$), 7.22 (s, 2, CHdCH). $^{13}$C NMR CDCl$_3$, 125.70 MHz): δ 137.26 (ipso-C$_6$H$_5$), 128.64 (CHdCH), 128.63 (m-C$_6$H$_5$), 127.56 (p-C$_6$H$_5$), 126.47 (o-C$_6$H$_5$). LRMS (EI): calcd for C$_{14}$H$_{12}$ 77Z/z 180, found m/z 180.

4-Acetylstilbene (Y=C(O)Me). $^1$H NMR (CDCl$_3$, 500 MHz): δ 7.93 (d, 2, o-C$_6$H$_4$C(O)Me, J$_{HH}$) 8), 7.54 (d, 2, J$_{HH}$=8), 7.52 (d, 2, J$_{HH}$=8), 7.37 (t, 2, m-C$_6$H$_5$, J$_{HH}$=7.5), 7.30 (t, 1, P—C$_6$H$_5$, J$_{HH}$=7), 7.19 (d, 1, CHdCH, 3 J$_{HH}$=16.5), 7.09 (d, 1, CHdCH, 3 J$_{HH}$=16.5), 2.57 (s, 3, Me). $^{13}$C NMR (CDCl$_3$, 125.70 MHz): δ 197.18 (CdO), 141.70 (C), 136.43 (C), 135.66 (C), 131.17 (CH), 128.63 (CH), 128.58 (CH), 128.10 (CH), 127.16 (CH), 126.63 (CH), 126.27 (CH), 26.33 (CH$_3$). Anal. Calcd for C$_{16}$H$_{14}$O: C, 86.45; H, 6.35. Found: C, 86.12; H, 6.40.

4-Nitrostilbene (Y=NO2). $^1$H NMR (CDCl$_3$, 500 MHz): δ 8.21 (d, 2, o-C6H4NO2, J$_{HH}$=8.5), 7.62 (d, 2, m-C6H4NO2, J$_{HH}$=8.5), 7.56 (d, 2, o-C6H5CHdCH, J$_{HH}$=7.5), 7.41 (t, 2, m-C$_6$H$_5$CHdCH, J$_{HH}$=7.5), 7.35 (t, 1, p-C6H5CHdCH, J$_{HH}$=7), 7.27 (d, 1, CHdCH, 3 J$_{HH}$=16), 7.14 (d, 1, CHdCH, 3 J$_{HH}$=16). $^{13}$C NMR (CDCl$_3$, 125.70 MHz): δ 146.65 (CNO2), 143.76 (C), 136.09 (C), 133.21 (CH), 128.82 (CH), 128.77 (CH), 126.95 (CH), 126.77 (CH), 126.18 (CH), 124.05 (CH). LRMS (EI): calcd for C$_{14}$H$_{11}$NO$_2$ m/z 225, found m/z 225. Anal. Calcd for C$_{14}$H$_{11}$NO$_2$: C, 74.65; H, 4.92; N, 6.22. Found: C, 74.35; H, 4.98; N, 6.16.

4-Stilbenecarboxaldehyde (Y=CHO). $^1$H NMR (CDCl$_3$, 500 MHz): δ 9.98 (s, 1, CHO), 7.86 (d, 2, o-C$_6$H$_4$CHO, J$_{HH}$=8.5), 7.63 (d, 2, m-C$_6$H$_4$CHO, J$_{HH}$=8.5), 7.54 (d, 2, o-C$_6$H$_5$CHdCH, J$_{HH}$=7.5), 7.39 (t, 2, m-C$_6$H$_5$CHdCH, J$_{HH}$=7.5), 7.32 (t, 1, p-C$_6$H$_5$CHdCH, J$_{HH}$=7), 7.24 (d, 1, CHdCH, J$_{HH}$=16.5), 7.12 (d, 1, CHdCH, J$_{HH}$=16.5). $^{13}$C NMR (CDCl$_3$, 125.70 MHz): δ 191.47 (CHO), 143.22 (C), 136.37 (C), 135.14 (C), 132.01 (CH), 130.07 (CH), 128.69 (CH), 128.37 (CH), 127.14 (CH), 126.78 (CH), 126.75 (CH). LRMS (EI): Calcd for C$_{15}$H$_{12}$O m/z 208, found m/z 208.

While embodiments of the present invention have been illustrated and described, various modifications and improvements can be made by persons skilled in the art. The embodiments of the present invention are therefore described in an illustrative but not restrictive sense. It is intended that the present invention is not limited to the particular forms as illustrated, and that all the modifications not departing from the spirit and scope of the present invention are within the scope as defined in the appended claims.

What is claimed is:

1. A metal complex comprising a ligand L and a metal center M$^1$, wherein

M$^1$ is selected from the group consisting of transition metal, Li, Na, K, Mg, Ca, Al, and Ga; and the ligand L is represented by the following general formula I

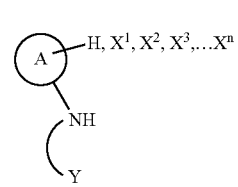

formula I (a) wherein:

A represents a ring or heterocyclic ring, and said ring or heterocyclic ring is unsubstituted or substituted with X$^1$ to X$^n$;

$X^1$ to $X^n$, for each occurrence independently represent one or more groups selected from the group consisting of hydrocarbons, $PR^1R^2$, $NR^1R^2$, $OR^1$, $SR^1$, and $AsR^1R^2$;

Y represents a group selected from the group consisting of $PR^1R^2$, $NR^1R^2$, $OR^1$, $SR^1$, and $AsR^1R^2$;

n represents an integer larger than or equal to 1;

$R^1$ and $R^2$ for each occurrence independently represent saturated or unsaturated hydrocarbon or aromatic groups with or without heteroatoms of O, S, N, P or As; and the linkage between N—Y is a saturated or unsaturated hydrocarbon or aromatic group with or without substituent; and (b) wherein:
the metal complex is not [NP]Li(THF)$_2$;[Me-NP]Li(THF)$_2$;[PNP]Li(THF)$_2$;[Me-MP]Ni($\eta_3$-CH$_2$Ph).

2. The complex according to claim 1, wherein A is an unsubstituted or substituted heterocyclic ring comprising N, O, S, or P atom.

3. The complex according to claim 2, wherein A is a five or six membered ring or a five or six membered heterocyclic ring.

4. The complex according to claim 1, wherein A is an unsubstituted or substituted aromatic ring.

5. The complex according to claim 4, wherein A is an unsubstituted or substituted phenyl group.

6. The complex according to claim 1, wherein A is an unsubstituted ring.

7. The complex according to claim 1, wherein A is a bicyclic or polycyclic ring.

8. The complex according to claim 1, wherein $X^1$ to $X^n$ are $PR^1R^2$.

9. The complex according to claim 1, wherein Y is $PR^1R^2$.

10. The complex according to claim 1, wherein $R^1$ and $R^2$ for each occurrence independently represent phenyl group with or without substituents.

11. The complex according to claim 1, wherein n is 1.

12. The complex according to claim 1, wherein the linkage between N—Y is alkyl with or without substituents.

13. The complex according to claim 12, wherein the linkage between N—Y is ethyl or propyl group with or without substituent.

14. The complex according to claim 1, wherein the linkage between N—Y is phenyl group with or without substituents.

15. The complex according to claim 1, wherein the ligand is a monoanion when H atom is absent from NH.

16. The complex according to claim 1, (a) wherein the ligand is bis(2-diphenylphosphinophenyl)amine represented by the following formula Ia:

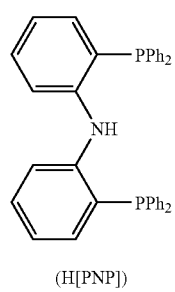

(H[PNP])

wherein Ph represents phenyl group; and (b) wherein the metal complex is not ]PNP]Li(THF)$_2$.

17. The complex according to claim 1, (a) wherein the ligand is N-(2-diphenylphosphinophenyl)-2,6-diisopropylaniline or N-(2-diphenylphosphinophenyl)-2,6-dimethylaniline represented by the following formula Ib represent:

formula Ib

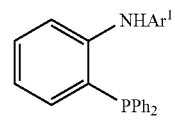

(H[NP], H[$^i$Pr-NP]) or (H[Me-NP])

wherein:
Ar$^1$ represents 2,6-C$_6$H$_3^i$Pr$_2$ or 2,6-C$_6$H$_3$Me$_2$;
Ph represents phenyl group; and
$^i$Pr represents isopropyl group; and (b) wherein the metal complex is not [Me-NP]Ni($\eta_3$-(H$_2$Ph).

18. The complex according to claim 1, wherein M$^1$ is selected from the group consisting of Zn, Pd, Al, and Ni.

19. The complex according to claim 1, wherein the ligand is coordinated to the metal center through two coordinate bonds, and the complex is represented by the following general formula V:

$$L_b M^1 Z^1_C \qquad \text{formula V}$$

wherein:
the number of ligand L is b;
the number of Z$^1$ is C;
the number of the coordination number of M$^1$ is a; and
Z$^1$ is coordinated to metal M$^1$ through d coordinate bonds;
Z$^1$ represents a group;
$2b+cd \leq a$; and
the linkage between L and M$^1$ is represented by the following general formula Va:

formula Va

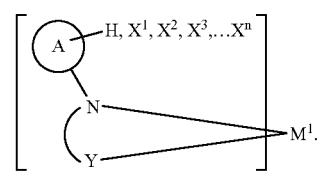

20. The complex according to claim 19, wherein Z$^1$ is selected from the group consisting of an unsubstituted or substituted hydrocarbon group, unsubstituted or substituted aromatic group, halogen group and ligand L.

21. The complex according to claim 19, wherein Z$^1$ represents ligand L.

22. The complex according to claim 19 which is represented by the following formula Vb;

formula Vb ([NP]$_2$Zn)

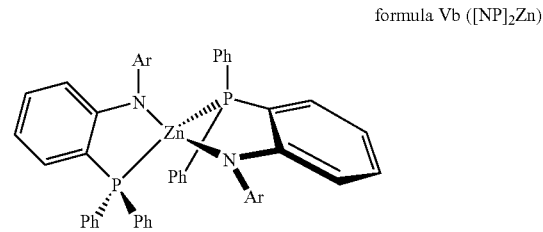

wherein:

$Ar^2$ represents $2,6\text{-}C_6H_3{}^iPr_2$;

Ph represents phenyl group; and $^iPr$ represents isopropyl group.

23. The complex according to claim 19 which is represented by the following formula Vc;

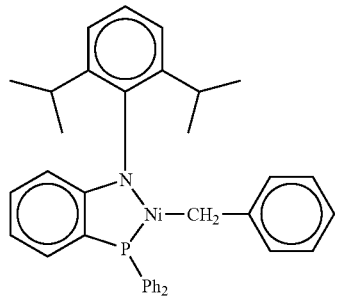

formula Vc wherein Ph represents phenyl group.

24. The complex according to claim 19 which is represented by the following general formula Vd;

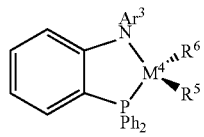

formula Vd wherein $Ar^3$ represents $2,6\text{-}C_6H_3{}^iPr_2$ or $2,6\text{-}C_6H_3Me_2$;

$^iPr$ represents isopropyl group;

$R^5$ and $R^6$ independently represent methyl group, ethyl group, $CH_2SiMe_3$, phenyl group, $PMe_3$, or halogen; and $R^5$ and $R^6$ taken together optionally represent the group represented by the following formula VII; and

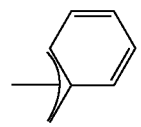

formula VII $M^4$ represents the metal center of Ni or Al.

25. The complex according to claim 1, wherein the ligand is coordinated to the metal center through three coordinate bonds, the complex is represented by the following general formula VI:

 formula VI wherein:

the number of ligand L is e;

the number of $Z^2$ is f;

the number of the coordination number of $M^1$ is a; and $Z^2$ is coordinated to metal $M^1$ through g coordinate bonds;

$Z^2$ represents a group;

$3e+fg \leqq a$; and the linkage between L and $M^1$ is represented by the following general formula VIa:

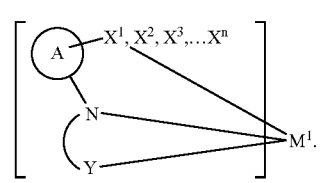

formula VIa

26. The complex according to claim 25, wherein $Z^2$ is selected from the group consisting of an unsubstituted or substituted hydrocarbon group, unsubstituted or substituted aromatic group, halogen group and ligand L.

27. The complex according to claim 25, wherein $Z^2$ represents ligand L.

28. The complex according to claim 25 represented by the following general formula VIb;

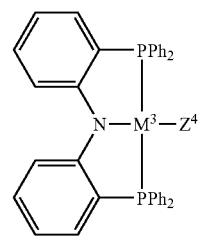

formula VIb wherein $M^3$ represents Ni or Pd;

$Z^4$ represents a group;

Ph represents phenyl group.

29. The complex according to claim 28, $Z^4$ is selected from the group consisting of an unsubstituted or substituted hydrocarbon group, unsubstituted or substituted aromatic group, and halogen group.

30. The complex according to claim 28, $Z^4$ is selected from the group consisting of methyl, ethyl, n-butyl, i-butyl, $CH_2SiMe_3$, Cl, OAc and phenyl group.

31. A method for synthesizing the complex according to claim 1 comprising reacting $M^1E$ and the ligand L to form the complex:

scheme VII

wherein:

E represents alkyl, aryl, amide, or alkoxide group.

32. The method according to claim 31 comprising the steps of:

(a) reacting $M^5E$ and the ligand to eliminate HE and form the complex $[M^5L]$; and scheme VIII

(b) reacting $[M^5L]$ and $M^1Hal^6$ to form $[M^1L]$;

wherein:

M⁵ is selected from the group consisting of transition metal, Li, Na, K, Mg, Ca, Al, and Ga;

E represents alkyl, aryl, amide, or alkoxide group; and $Hal^6$ represents halogen.

33. The method according to claim 31 comprising the steps of:
(a) reacting the ligand L and $M^1Z^3$ to form $LM^1Z^3$ in the presence of diethyl ether or THF; and
(b) reacting the ligand L and $LM^1Z^3$ by heat to form $L_2M^1$, wherein $Z^3$ represents a group.

34. The method according to claim 33, $Z^3$ is selected from the group consisting of an unsubstituted or substituted hydrocarbon group, or unsubstituted or substituted aromatic group, and halogen group.

35. The method according to claim 34, $Z^3$ is methyl group or ethyl group.

36. The method for synthesizing the complex according to claim 31 comprising the steps of:
(a) reacting the ligand L and n-butyllithium to form $LLi(THF)_2$ in the presence of THF; and
(b) reacting $LLi(THF)_2$ and $M^1Cl_2$ to form $LM^1$.

37. The method according to claim 31 comprising the steps of:
(a) reacting the ligand L and n-butyllithium to form $LLi(THF)_2$ in the presence of THF;
(b) reacting $LLi(THF)_2$ and $M^1Cl_2(DME)$ to form $LM^1Cl$; and
(c) reacting $LM^1Cl$ and $Z^1MgCl$ or $Z^2MgCl$ to form $LM^1Z^1$ or $LM^1Z_2$, wherein $Z^1$ or $Z^2$ represents a group.

38. The method for synthesizing the complex according to claim 31 comprising the steps of:
(a) reacting the ligand L and n-butyllithium to form $LLi(THF)_2$ in the presence of THF;
(b) reacting $LLi(THF)_2$ and $M^1Cl_3$ in the presence of toluene to form $LM^1Cl_2$; and
(c) reacting $LM^1Cl_2$ and $LiZ^1$ or $LiZ^2$ to form the complex, wherein $Z^1$ or $Z^2$ represents a group.

* * * * *